United States Patent
Beinlich et al.

(10) Patent No.: US 7,081,476 B2
(45) Date of Patent: Jul. 25, 2006

(54) TOCOPHEROL ENRICHED COMPOSITIONS FOR REDUCING IL6 LEVELS

(75) Inventors: Peggy Beinlich, San Mateo, CA (US); Sekhar Boddupalli, San Jose, CA (US); Lesley A. Brown, Reno, NV (US); Darlene M. Dreon, Menlo Park, CA (US); Stephen Flaim, San Diego, CA (US); Guy Miller, San Jose, CA (US); Stephen D. Phinney, Elk Grove, CA (US)

(73) Assignee: Galileo Pharmaceuticals, Inc., Santa Clara, CA (US)

( * ) Notice: Subject to any disclaimer, the term of this patent is extended or adjusted under 35 U.S.C. 154(b) by 0 days.

(21) Appl. No.: 11/038,373

(22) Filed: Jan. 18, 2005

(65) Prior Publication Data

US 2005/0124689 A1 Jun. 9, 2005

Related U.S. Application Data

(63) Continuation of application No. 10/227,094, filed on Aug. 21, 2002.

(60) Provisional application No. 60/314,257, filed on Aug. 21, 2001, provisional application No. 60/314,256, filed on Aug. 21, 2001, provisional application No. 60/314,223, filed on Aug. 21, 2001.

(51) Int. Cl.
*A61K 31/355* (2006.01)

(52) U.S. Cl. .................................. 514/458

(58) Field of Classification Search ............. 514/458
See application file for complete search history.

(56) References Cited

U.S. PATENT DOCUMENTS

| | | | |
|---|---|---|---|
| 4,325,965 A | 4/1982 | Chiba | 424/284 |
| 5,139,796 A | 8/1992 | Barkalow et al. | 426/3 |
| 5,200,214 A | 4/1993 | Barkalow et al. | 426/3 |
| 5,252,604 A | 10/1993 | Nagy et al. | 514/559 |
| 5,484,816 A | 1/1996 | Yanagida et al. | 514/725 |
| 5,804,168 A | 9/1998 | Murad | 424/59 |
| 5,961,993 A | 10/1999 | Boussouira et al. | 424/101 |
| 6,024,941 A | 2/2000 | Yanagida et al. | 424/59 |
| 6,024,960 A | 2/2000 | Kharazmi et al. | 424/195.1 |
| 6,048,891 A | 4/2000 | Wechter | 514/456 |
| 6,239,171 B1 | 5/2001 | Lane et al. | 514/458 |
| 6,242,479 B1 | 6/2001 | Wechter | 514/456 |
| 6,346,544 B1 | 2/2002 | Hensley et al. | 514/458 |
| 6,410,589 B1 | 6/2002 | Wechter | 514/458 |
| 6,716,451 B1 | 4/2004 | Udell et al. | 424/455 |
| 6,780,886 B1 | 8/2004 | Kondo et al. | 514/456 |
| 2002/0006954 A1 | 1/2002 | Hensley et al. | 514/458 |
| 2002/0040053 A1 | 4/2002 | Kondo et al. | 514/456 |
| 2002/0143049 A1 | 10/2002 | Miller et al. | 514/458 |
| 2004/0082649 A1 | 4/2004 | Rich et al. | 514/458 |
| 2004/0106674 A1 | 6/2004 | Rich et al. | 514/458 |
| 2004/0116512 A1 | 6/2004 | Naguib et al. | 514/458 |

FOREIGN PATENT DOCUMENTS

| | | |
|---|---|---|
| WO | 96/19214 | 6/1996 |
| WO | 00/44375 A1 | 8/2000 |
| WO | 00/57876 | 10/2000 |
| WO | 01/02004 A1 | 1/2001 |

OTHER PUBLICATIONS

"Optimal Ratio Mixed Vitamin E Complex for Advanced Antioxidant Protection", *Metagenics Through Nutrition, Formula Focus*, MET181, Jul. 2001 (2 pgs.), 2001.

Upritchard, et al., "Effect of Supplementation With Tomato Juice, Vitamin E, and Vitamin C an LDL Oxidation and Products of Inflammatory Activity in Type 2 Diabetes", *Diabetes Care*, 23:733-738, 2000.

Akpolat, et al. (2000). "Effect of Vitamin E and Pentoifylline on Glycerol-induced Acute Renal Failure", *Nephron* 84:243-247.

Appenroth et al. (2001). "LLU-α, and Endogenous Metabolite of γ-Tocopherol, is More Effective Against Metal Nephrotoxicity in Rats Than γ-Tocopherol", *Toxicology Letters* 122:255-265.

Bieri & Evarts (1973). "Vitamin E Activity of γ-tocopherol in the Rat, Chick and Hamster", *J. Nutr.* 104:850-857.

Boaz, et al. (2000). "Secondary Prevention with Antioxidants of Cardiovascular Disease in Endstage Renal Disease" (SPACE): Randomised Placebo-Controlled Trial. *The Lancet* 356:1213-1218.

Chapkin, et al. (1983). "Effect of Vitamin E Supplementation on Serum and High-density Lipoprotein Cholesterol in Renal Patients on Maintenance Hemodialysis" *Am. J. Clin. Nutr.* 38:253-256.

(Continued)

*Primary Examiner*—Phyllis G. Spivack
(74) *Attorney, Agent, or Firm*—Foley & Lardner LLP

(57) ABSTRACT

Non-alpha-tocopherol enriched tocopherol compositions and non-alpha metabolite enriched compositions are disclosed for use in the reduction of the inflammatory marker IL-6.

20 Claims, No Drawings

OTHER PUBLICATIONS

Dillard, et al. (1983). "Relative Antioxidant Effectiveness of α-Tocopherol and γ-Tocopherol in Iron-Loaded Rats", *J. Nutr.* 113:226-227.

Fryer, Michael J (1999). "Treatment of Acute Renal Failure with Antioxidant Vitamin E", *Renal Failure* 21(2) 231-233.

Jiang, et al. (2000). "γ-Tocopherol and its major metabolite, in Contrast to α-Tocopherol, inhibit cyclooxygenease Activity in Macrophages and Epithelial Cells", *PNAS* 97(21): 11494-11499.

Jiang, et al. (2000). "γ-Tocopherol, the Major Form of Vitamin E in the US diet, Deserves More Attention". *Am. J. Clin. Nutr.* 74:714-722.

Kim, et al. (2000). "Vitamin E and Probucol Reduce Urinary Lipophilic Aldehydes and Renal Enlargement in Streptozotocin-induced Diabetic Rats". *Lipids* 35(11): 1225-1236.

L. Patrick and M. Uzick (2001) "Cardiovascular Disease: C-Reactive Protein and the Inflammatory Disease Paradigm: HMG-CoA Reductase Inhibitors, Alpha-tocopherol, Red Yeast Rice, and Olive Oil Polyphenols. A Review of the Literature" *Alternative Medicine Review* 6(3): 248-271.

Janet Raloff (2001). "Vitamin E Targets Dangerous Inflammation", *Science News* vol. 159, No. 15.

Sharma, et al. (1999). "Lipid Peroxide Levels in Chronic Renal Failure" *JAPI* 47(3):296-297.

Tepel, et al. (2002). "Antioxidative Therapie bei Gefaβ-und Nierenerkrankungen". *Medizinische Klink* 97: 144-151.

Vessby, et al. (2002). "Oxidative Stress and antioxidant Status in Type 1 Diabetes Mellitus", *J. Internal Med.* 251 :69-76.

Wijnen, et al. (2002). "Can Renal Dysfunction After Infrarenal Aortic Aneurysm Repair be Modified by Multi-antioxidant Supplementation?" *J. Cardiovasc. Surg.* 43:486-488.

Yuan, et al. (1994). "The Change of Intracellular Free Calcium Ion Concentration and Interleukin-1 Activity of Mononuclear Cells in Chronic Renal Failure Rats", *Chinese Journal of Pathophysiology*, 10(6):649-653.

TOCOPHEROL ENRICHED COMPOSITIONS FOR REDUCING IL6 LEVELS

CROSS-REFERENCE TO RELATED APPLICATIONS

This application is a continuation of pending application Ser. No. 10/227,094, filed Aug. 21, 2002 which claims benefit of U.S. Provisional Patent Application Ser. No. 60/314,257, filed Aug. 21, 2001, U.S. Provisional Patent Application Ser. No. 60/314,223, filed Aug. 21, 2001, and U.S. Provisional Patent Application Ser. No. 60/314,256, filed Aug. 21, 2001, all of which are incorporated by reference herein in their entirety.

TECHNICAL FIELD

This invention generally relates to non-alpha-tocopherol compositions such as gamma-tocopherol, beta-tocopherol or delta-tocopherol, and/or metabolite(s) thereof, and methods for treating and/or ameliorating the symptoms of inflammation in a mammalian subject. The invention also relates to methods of making such compositions.

BACKGROUND

Inflammation is an important component of host protection, and is a composite response including successive events in response to an injury which may be infectious or non-infectious. Inflammation involves a variety of events on the cellular, molecular and physiologic levels. These events include vasodilatation; increased vascular permeability; extravasation of plasma leading to interstitial edema; chemotaxis of neutrophils, macrophages and lymphocytes; cytokine production; acute phase reactants; leukocytosis; fever; increased metabolic rate; impaired albumin production and hypoalbuminemia; activation of complement; and stimulation of antibodies. Inflammation is associated with diseases or disorders such as, for example, neurodegenerative diseases, SIRS, asthma, diabetes associated nephropathy and retinopathy, protein wasting, muscle fatigue or inflammation and PMS, infectious diseases, as well as various cardiovascular disorders.

Biochemical markers of inflammation are known in the art and include C-reactive protein (CRP) and members of the interleukin family. The presence of elevated levels of certain of these markers has been shown to be associated with development of disease. For example, CRP has been reported as a marker for systemic inflammation Spanheimer (2001, *Postgrad. Med.* 109(4) 26) and Ridkler et al. (2000, *N.E.J. M.* 342(12):836–43).

U.S. Pat. Nos. 6,410,589; 6,242,479 and 6,048,891 disclose gamma-tocopherol compositions. U.S. Pat. No. 6,346,544 discloses desmethyl tocopherol compositions. U.S. Pat. No. 4,325,965 discloses the topical administration of delta-tocopherol for the treatment of psoriasis.

There remains a need for compositions and methods for reducing one or more biochemical markers of inflammation, thereby reducing or ameliorating the symptoms of inflammation associated with disease. Further, there remains a need for methods for reducing elevated CRP levels associated with a number of diseases and disorders including, but not limited to, cardiovascular disease, diabetes and infectious diseases.

The disclosure of all patents and publications cited herein are incorporated by reference in their entirety.

DISCLOSURE OF THE INVENTION

The present invention relates to non-alpha-tocopherol enriched tocopherol compositions and methods for treating and/or ameliorating the symptoms of inflammation in a mammalian subject.

The present invention provides methods of treating and/or ameliorating symptoms associated with non-cardiovascular inflammation in a mammalian subject, comprising administering to the subject a gamma-tocopherol enriched tocopherol composition in a pharmaceutically effective amount, and by said administering, reducing symptoms associated with said inflammation.

The present invention also provides methods of treating and/or ameliorating symptoms associated with non-cardiovascular inflammation in a mammalian subject, comprising administering to the subject a gamma-tocopherol metabolite enriched composition in a pharmaceutically effective amount, and by said administering, reducing symptoms associated with said inflammation. In preferred embodiments, the gamma-tocopherol metabolite is 2,7,8-trimethyl-2-(2'-carboxyethyl)-6-hydroxychroman (gamma-CEHC).

The present invention provides methods of treating and/or ameliorating symptoms associated with inflammation in a mammalian subject, comprising administering to the subject a beta-tocopherol enriched tocopherol composition in a pharmaceutically effective amount, and by said administering, reducing symptoms associated with said inflammation.

The present invention also provides methods of treating and/or ameliorating symptoms associated with inflammation in a mammalian subject, comprising administering to the subject a beta-tocopherol metabolite enriched composition in a pharmaceutically effective amount, and by said administering, reducing symptoms associated with said inflammation. In preferred embodiments, the beta-tocopherol metabolite is 2,5,8-trimethyl-2-(2-carboxyethyl)-6-hydroxychroman (beta-CEHC).

The present invention provides methods of treating and/or ameliorating symptoms associated with inflammation in a mammalian subject, comprising administering to the subject a delta-tocopherol enriched tocopherol composition in a pharmaceutically effective amount, and by said administering, reducing symptoms associated with said inflammation, wherein said administration specifically excludes topical administration of delta-tocopherol enriched tocopherol compositions for the treatment of psoriasis as described in U.S. Pat. No. 4,325,965; but does encompasses systemic administration of delta-tocopherol enriched tocopherol compositions for the treatment of psoriasis; and does encompasses topical administration of delta-tocopherol enriched tocopherol compositions for non-psoriatic dermal conditions, diseases or disorders.

The present invention also provides methods of treating and/or ameliorating symptoms associated with inflammation in a mammalian subject, comprising administering to the subject a delta-tocopherol metabolite enriched composition in a pharmaceutically effective amount, and by said administering, reducing symptoms associated with said inflammation. In preferred embodiments, the delta-tocopherol metabolite is 2,8,-dimethyl-2-(2-carboxyethyl)-6-hydroxychroman (delta-CEHC).

The present invention also provides methods for reducing the levels of inflammatory markers and proteins associated with inflammation, such as for example, CRP; cytokines associated with inflammation, including IL-1 through 17;

TNF-α; and B61; and methods of reducing pain associated with inflammation and/or reducing edema associated with inflammation.

The present invention provides methods of reducing the level of C-reactive protein (CRP) in an individual subject to a CRP associated inflammatory condition comprising administering to the individual an effective amount of a non-alpha-tocopherol enriched tocopherol composition. In some examples, the non-alpha-tocopherol is selected from the group consisting of gamma-tocopherol or a gamma-tocopherol metabolite thereof, beta-tocopherol or a beta-tocopherol metabolite thereof, and delta-tocopherol or a delta-tocopherol metabolite thereof. In other examples, the non-alpha-tocopherol is gamma-tocopherol or a gamma-tocopherol metabolite, such as for example, gamma-CEHC. In further examples, the non-alpha-tocopherol is beta-tocopherol or a beta-tocopherol metabolite, such as for example, beta-CEHC. In additional examples, the non-alpha-tocopherol is delta-tocopherol or a delta-tocopherol metabolite, such as delta-CEHC.

The present invention provides methods of reducing the level of an inflammatory marker in an individual subject to end-stage renal disease comprising administering to the individual a non-alpha-tocopherol enriched tocopherol composition in an effective amount. In some examples, the inflammatory marker is CRP or IL-6. In other examples, the non-alpha-tocopherol is gamma-tocopherol. In further examples, the gamma-tocopherol enriched tocopherol composition comprises at least 60% gamma-tocopherol, at least 70% gamma-tocopherol, at least 80% gamma-tocopherol or at least 90% gamma-tocopherol. In further examples, the gamma-tocopherol enriched tocopherol composition comprises at least 60% gamma-tocopherol, and at least 28% delta-tocopherol.

The present invention provides methods for ameliorating a symptom of an inflammatory condition in an individual subject to an inflammatory condition comprising administering to the individual a gamma-tocopherol enriched tocopherol composition in an amount effective to reduce the level of an inflammatory marker associated with said inflammatory condition. In some examples, the inflammatory marker is CRP or IL-6. In other embodiments, the inflammatory condition is selected from the group consisting of a respiratory inflammatory condition, sepsis, diabetes, muscle fatigue, systemic lupus erythematosis (SLE), end stage renal disease (ESRD), and periodontal disease.

The present invention also provides methods for ameliorating a symptom of an inflammatory condition in an individual subject to an inflammatory condition comprising administering to the individual a beta-tocopherol enriched tocopherol composition in an amount effective to reduce the level of an inflammatory marker associated with said inflammatory condition. In some examples, the inflammatory marker is CRP or IL-6. In other examples, the inflammatory condition is selected from the group consisting of a respiratory inflammatory condition, sepsis, diabetes, muscle fatigue, SLE, renal inflammation including ESRD, periodontal disease and inflammatory skin conditions.

The present invention also provides methods for ameliorating a symptom of an inflammatory condition in an individual subject to an inflammatory condition comprising administering to the individual a delta-tocopherol enriched tocopherol composition in an amount effective to reduce the level of an inflammatory marker associated with said inflammatory condition. In some examples, the inflammatory marker is CRP or IL-6. In other examples, the inflammatory condition is selected from the group consisting of a respiratory inflammatory condition, sepsis, diabetes, muscle fatigue, SLE, renal inflammation including ESRD, periodontal disease and non-psoriatic inflammatory skin conditions.

In other examples, the non-alpha-tocopherol enriched tocopherol compositions or non-alpha-tocopherol metabolite enriched compositions of the present invention may be nutraceutical or pharmaceutical compositions and may further comprise a nutraceutically acceptable carrier or a pharmaceutically acceptable carrier.

The present invention also provides methods for making the non-alpha-tocopherol enriched tocopherol compositions or non-alpha-tocopherol metabolite enriched compositions of the present invention.

BRIEF DESCRIPTION OF THE DRAWINGS

Not Applicable

BEST MODE FOR CARRYING OUT THE INVENTION

The present invention provides non-alpha-tocopherol enriched tocopherol compositions, non-alpha-tocopherol metabolite enriched compositions and methods for using such compositions in the treatment and/or amelioration of a symptom of inflammation or a symptom of an inflammatory condition and/or for reducing the level of an inflammatory marker associated with inflammation or an inflammatory condition and/or for reducing a symptom associated with inflammation or an inflammatory condition, such as pain and edema. In some examples, the present invention provides compositions and methods for reducing one or more biochemical markers of inflammation, including for example reducing CRP or reducing IL-6, thereby ameliorating an inflammatory symptom associated with disease or an inflammatory condition and/or reducing a mammalian subject's risk of progressing into long term or chronic inflammatory conditions. In some examples, the present invention provides compositions and methods for maintaining normal or healthy levels of inflammatory markers in subjects.

Inflammation is associated with for example, cardiovascular diseases or disorders; neurodegenerative diseases such as, Alzheimers; infectious disease, such as, for example, myocarditis, cardiomyopathy, acute endocarditis, pericarditis; atherosclerosis; Systemic Inflammatory Response Syndrome (SIRS)/sepsis; adult respiratory distress syndrome (ARDS); asthma; rheumatoid arthritis, osteoarthritis, systemic lupus eryhematosis; Airway hyperresponsiveness (AHR); bronchial hyperreactivity; Chronic Obstructive Pulmonary disease (COPD); Congestive Heart Failure (CHF); inflammatory complications of diabetes mellitus; end stage renal disease (ESRD), pre-menstrual syndrome (PMS) or muscle fatigue or inflammation; and dermal conditions.

A number of proximal mediators of the inflammatory response have been identified and include the inflammatory cytokines, interleukin-1 through 17, including interleukin-1β (IL-1β), as described in U.S. Pat. No. 6,210,877, and tumor necrosis factor alpha (TNF-α), as described in U.S. Pat. Nos. 5,993,811 6,210,877 and 6,203,997. Other molecules have been reported for use as markers of systemic inflammation, including for example, CRP (Ridker et al. supra; Spanheimer supra); certain cellular adhesion molecules such as e-selectin (also known as ELAM), sICAM-1 (U.S. Pat. No. 6,049,147), integrins, ICAM-1, ICAM-3, BL-CAM, LFA-2, VCAM-1, NCAM, PECAM, and neopterin; and B61 (U.S. Pat. No. 5,688,656). Other markers associated with inflammation include leukotriene, thromboxane, and isoprostane. Other proteins or markers associated with inflammation include serum amyloid A protein, fibrinectin, fibrinogen, leptin, prostaglandin E2, serum procalcitonin, soluble TNF receptor 2, and elevated white blood count, including percent and total granulocytes (polymorphonuclear leukocytes) monocytes, lymphocytes and eosinophils.

The present invention provides non-alpha-tocopherol enriched tocopherol compositions and non-alpha-tocopherol metabolite enriched compositions and methods for reducing the level of an inflammatory marker associated with inflammation, such as for example, CRP; a cytokine associated with inflammation, including IL-1 through IL-17 and in some examples, IL-6; TNF-α; and B61; and methods for reducing a symptom associated with inflammation such as for example, reducing pain, and/or reducing edema and/or reducing fatigue associated with inflammation.

In some examples, the present invention provides methods of reducing elevated levels of CRP associated with inflammation in a mammalian subject comprising administering to the subject a non-alpha-tocopherol enriched tocopherol composition or a non-alpha-tocopherol metabolite enriched composition in a pharmaceutically effective amount, and by said administering, reducing said elevated levels of CRP associated with said inflammation in said subject.

In other examples, the present invention provides methods for maintaining healthy or normal levels of C-Reactive Protein (CRP) in a mammalian subject at risk for inflammation or an inflammatory condition(s) associated with the diseases or disorders disclosed herein, comprising administering to the subject a non-alpha-tocopherol enriched tocopherol composition or a non-alpha-tocopherol metabolite enriched composition in a pharmaceutically effective amount, and by said administering, maintaining healthy or normal levels of CRP in said mammalian subject.

Definitions

Inflammation is associated with diseases, disorders and conditions such as for example, cardiovascular diseases or disorders; neurodegenerative diseases such as, Alzheimers; infectious diseases, such as, for example, myocarditis, cardiomyopathy, acute endocarditis, pericarditis; atherosclerosis; Systemic Inflammatory Response Syndrome (SIRS)/sepsis; adult respiratory distress syndrome (ARDS); asthma; rheumatoid arthritis, osteoarthritis, systemic lupus eryhematosis; Airway hyperresponsiveness (AHR); bronchial hyper-reactivity; Chronic Obstructive Pulmonary disease (COPD); Congestive Heart Failure (CHF); inflammatory complications of diabetes mellitus; ESRD; pre-menstrual syndrome (PMS); muscle fatigue or inflammation and dermal conditions. As used herein, "respiratory inflammatory conditions" refer to SIRS, ARDS, asthma and AHR.

Elevated levels of C-reactive protein (CRP) have been associated with various inflammatory conditions. As used herein, "CRP associated inflammation" refers to inflammatory conditions and/or inflammation associated with elevated levels of CRP such as for example, cardiovascular diseases or disorders, including atrial fibrillation, unstable angina, coronary artery disease, peripheral artery disease, cardiac allograft vasculopathy (CAVD); mastitis; preclampsia; inflammatory bowel conditions; stroke; tissue infarction; lumbosciatic; estrogen/progestin hormone replacement therapy (HRT); infection (bacterial, viral and protozoan); bacterial meningitis; trauma; surgery; biomaterial implants; smoking; obesity; neurodegenerative diseases such as, Alzheimers; infectious disease, such as, for example, myocarditis, cardiomyopathy, acute endocarditis, pericarditis; atherosclerosis; Systemic Inflammatory Response Syndrome (SIRS)/sepsis; adult respiratory distress syndrome (ARDS); asthma; rheumatoid arthritis, osteoarthritis, systemic lupus erythematosis; Airway hyper-responsiveness (AHR); bronchial hyper-reactivity; Chronic Obstructive Pulmonary disease (COPD); Congestive Heart Failure (CHF); inflammatory complications of diabetes mellitus type I and type II; metabolic syndrome; end stage renal disease (ESRD), pre-menstrual syndrome (PMS) or muscle fatigue or inflammation; multiple organ dysfunction syndrome (MODS); airway hyper-responsiveness (AHR); bronchial hyper-reactivity; aging; acute allergic reactions; gingivitis and dermal conditions.

As used herein, "cardiovascular disease" includes diseases associated with the cardio-pulmonary and circulatory systems including but not limited to ischemia, angina, edematous conditions, artherosclerosis, LDL oxidation, adhesion of monocytes to endothelial cells, foam-cell formation, fatty-streak development, platelet adherence, and aggregation, smooth muscle cell proliferation, reperfusion injury, high blood pressure, and thrombolic disease.

As used herein, "markers associated with inflammation" include, but are not limited to CRP, cytokines associated with inflammation, such as members of the interleukin family, including IL-1 through IL-17 that are associated with inflammation, TNF-α; B61; certain cellular adhesion molecules, such as for example, e-selectin (also known as ELAM), sICAM, integrins, ICAM-1, ICAM-3, BL-CAM, LFA-2, VCAM-1, NCAM and PECAM; neopterin; serum procalcitonin; leukotriene, thromboxane, and isoprostane. In particular, elevated levels of CRP are associated with cardiovascular diseases and disorders, infectious diseases, such as, myocarditis, cardiomyopathy, acute endocarditis, or pericarditis; SIRS; diabetes; PMS; and systemic inflammation. Elevated levels of cellular adhesion molecules are associated with systemic inflammation. Elevated levels of IL-1 and TNF-α are associated with IDDM and NDDM associated inflammation. Elevated levels of IL-10 and IL-6 are associated with SIRS. Elevated levels of neopterin are associated with SIRS. Elevated levels of procalcitonin are associated with systemic inflammation. Other proteins or markers associated with inflammation include serum amyloid A protein, fibrinectin, fibrinogen, leptin, prostaglandin E2, serum procalcitonin, soluble TNF receptor 2, and elevated white blood count, including percent and total granulocytes (polymorphonuclear leukocytes)m monocytes, lymphocytes and eosinophils.

By "tocopherol" is meant any of a family of molecules which are characterized by a 6-chromanol ring structure and a side chain at the 2 position. A "non-alpha-tocopherol enriched tocopherol composition", as used herein refers to the non-alpha-tocopherol, such as for example, gamma-, beta- or delta-tocopherol as being enriched with respect to total tocopherols in the composition. Tocopherols possess a 4',8',12'-trimethyltridecyl phytol side chain. As used herein, the term "tocopherol" encompasses, but is not limited to:

alpha-tocopherol, [2R-2R*(4R*,8R*)]-3,4-dihydro-2,5,7,8-tetramethyl-2-(4,8,12-trimethyltridecyl)-2H-1-benzopyran-6-ol; 2,5,7,8-tetramethyl-2-(4',8',12'-trimethyltridecyl)-6-chromanol; 5,7,8-trimethyltocol, Fernholz (1937) *J. Am. Chem. Soc.* 59:1154 and 60:700;

beta-tocopherol, 3,4-dihydro-2,5,8-trimethyl-2-(4,8,12-trimethyltridecyl)-2H-1-benzopyran-6-ol; 2,5,8-trimethyl-2-(4,8,12-trimethyltridecyl)-6-chromanol; 5-8-dimethyltocol; cumotocopherol; neotocopherol; p-xylotocopherol;

gamma-tocopherol, 3,4-dihydro-2,7,8-trimethyl-2-(4,8,12-trimethyltridecyl)-2H-1-benzyopyran-6-ol; 2,7,8-trimethyl-2-(4,8,12-trimethyltridecyl)-6-chromanol; 7,8-dimethyltocol; o-xylotocopherol;

delta-tocopherol, [2R-[2R*(4R*,8R*)]]-3,4-dihydro-2,8-dimethyl-2-(4,8,12-trimethyltridecyl)-2H-1-benzo-pyran-6-ol; 8-methyltocol;

epsilon-tocopherol, [R-(E,E)]-3,4-dihydro-2,5,8-trimethyl-2-(4,8,12-trimethyl-3,7,11-tridecatrienyl)-2H-1-benzopyran-6-ol; 2,5,8-trimethyl-2-(4,8,12-trimethyltrideca-3,7,11-trienyl)chroman-6-ol; 5-methyltocol;

$zeta_1$-tocopherol, 3,4-dihydro-2,5,7,8-tetramethyl-2-(4,8,12-trimethyl-3,7,11-tridecatrienyl)-2H-1-benzopyran-6-ol; 2,5,7,8-tetramethyl-2-(4,8,12-trimethyl-3,7,11-tridecatrienyl)-6-chromanol; 5,7,8-trimethyltocotrien-3',7',11'-ol;

$zeta_2$-tocopherol, 3,4-dihydro-2,5,7-trimethyl-2-(4,8,12-trimethyltridecyl)-2H-1-benzopyran-6-ol; 2,5,7-trimethyl-2-(4,8,12-trimethyltridecyl-6-chromanol; 5,7-dimethyltocol; and eta-tocopherol, 3,4-dihydro-2,7-dimethyl-2-(4,8,12-trimethyltridecyl)-2H-1-benzopyran-6-ol; 2,7-dimethyl-2-(4,8,12-trimethyltridecyl)-6-chromanol; 7-methyltocol. See *The Merck Index* (1996), Twelfth Edition, Merck & Co., Whitehouse Station, N.J., pp. 1620–1621 and 1712, and references cited therein. Other tocopherols include $xi_1$-, $xi_2$-, and sigma-tocopherols.

Generally speaking, commercially available dietary supplements of Vitamin E are alpha-tocopherol enriched compositions. As used herein, a "non-alpha-tocopherol enriched tocopherol composition" refers to a composition comprising at least 50% of any tocopherol except for alpha-tocopherol. In some examples, the non-alpha-tocopherol is gamma-tocopherol, or a metabolite thereof, beta-tocopherol, or a metabolite thereof, or delta-tocopherol or a metabolite thereof. A non-alpha tocopherol enriched tocopherol composition may comprise a mixture of tocopherols, including alpha-tocopherol, as long as the composition comprises at least 50% of a non-alpha tocopherol. As used herein, a "non-alpha-tocopherol metabolite" refers to a metabolite of a non-alpha-tocopherol, such as for example, a gamma-tocopherol metabolite, such as gamma-CEHC; a beta-tocopherol metabolite, such as for example, beta-CEHC; or a delta-tocopherol metabolite, such as for example, delta-CEHC.

In the body of a subject, a non-alpha-tocopherol breaks down into metabolites. The present invention encompasses the use of gamma-tocopherol enriched tocopherol compositions that further comprise a gamma-tocopherol metabolite such as 2,7,8-trimethyl-2-(beta-carboxyethyl)-6-hydroxychroman (gamma-CEHC), racemic gamma-CEHC and (S) gamma-CEHC. See for example, Wechter et al., U.S. Pat. No. 6,242,479 for disclosure of gamma-tocopherol metabolites, specifically incorporated herein by reference in its entirety. The present invention also encompasses the use of gamma-tocopherol metabolite enriched compositions that further comprise gamma-tocopherol.

The present invention encompasses the use of beta-tocopherol enriched tocopherol compositions that further comprise a beta-tocopherol metabolite such as 2,5,8-trimethyl-2-(2-carboxyethyl)-6-hydroxychroman (beta-CEHC). The present invention also encompasses the use of beta-tocopherol metabolite enriched compositions that further comprise beta-tocopherol.

The present invention encompasses the use of delta-tocopherol enriched tocopherol compositions that further comprise a delta-tocopherol metabolite such as 2,8-dimethyl-2-(2-carboxyethyl)-6-hydroxychroman (delta-CEHC). The present invention also encompasses the use of delta-tocopherol metabolite enriched compositions that further comprise delta-tocopherol.

By a "non-tocopherol" is meant any compound which is not a tocopherol, tocotrienol, or derivative thereof, or the like.

By "non-naturally-occurring composition" is meant a composition which is not found in this form in nature. A non-naturally-occurring composition can be derived from a naturally-occurring composition, e.g., as non-limiting examples, via purification, isolation, concentration, chemical modification (e.g., addition or removal of a chemical group), and/or, in the case of mixtures, addition or removal of ingredients or compounds. A non-naturally-occurring composition can comprise or be derived from a non-naturally-occurring combination of naturally-occurring compositions. Thus, a non-naturally-occurring composition can comprise a mixture of purified, isolated, modified and/or concentrated naturally-occurring compositions, and/or can comprise a mixture of naturally-occurring compositions in forms, concentrations, ratios and/or levels of purity not found in nature.

"Agents" or "cytoprotective agents" are defined herein as compounds, mixtures, or formulations of compounds which are capable of treating or ameliorating the symptoms of inflammation, such as by reducing the levels of inflammatory markers, e.g., CRP, cytokines associated with inflammation, such as members of the interleukin family, including IL-1 through 17 that are associated with inflammation, TNF-α; B61; certain cellular adhesion molecules, such as for example, e-selectin (also known as ELAM), sICAM, integrins, ICAM-1, ICAM-3, BL-CAM, LFA-2, VCAM-1, NCAM and PECAM; neopterin; serum procalcitonin; leukotriene, thromboxane, isoprostane and/or by reducing pain and/or edema associated with the inflammation. Cytoprotective agents may provide cytoprotective activity prior to, simultaneous with and/or subsequent to the symptoms associated with inflammation.

As used herein, an agent is said to be "cytoprotective" or to have "cytoprotective property" or "cytoprotective activity" if administration of the agent reduces and/or ameliorates symptoms of inflammation and/or injury(ies) suffered by cells, tissues, organs and/or organisms that is associated with inflammation, such as for example, pain and/or edema. Cytoprotective activity and injury associated with inflammation can be quantified in assays which measure results of inflammation, such as elevated levels of CRP, cytokines associated with inflammation, such as members of the interleukin family, including IL-1 through 17 that are associated with inflammation, TNF-α; B61; certain cellular adhesion molecules, such as for example, e-selectin (also known as ELAM), sICAM, integrins, ICAM-1, ICAM-3, BL-CAM, LFA-2, VCAM-1, NCAM and PECAM; neopterin; serum procalcitonin; leukotriene, thromboxane, and isoprostane. Cytoprotective agents include cytoprotective amounts of a non-alpha-tocopherol, such as gamma-tocopherol, beta-tocopherol and delta-tocopherol and/or metabolites thereof.

By "amounts effective to reduce inflammation and/or symptoms due to inflammation" is meant that the cytoprotective agent or agents (e.g., a non-alpha-tocopherol and/or metabolites, thereof) is present in a final concentration sufficient for reducing inflammation, as measured by a reduction in an inflammatory marker, such as ELAM or an inflammatory cytokine, such as IL-6, or a reduction of CRP, and/or reduction of symptoms associated with inflammation, such as for example, pain and/or edema associated with inflammation. This amount includes, but is not limited to, a concentration which acts as a complete prophylaxis or treatment for a symptom of inflammation. An "effective amount" is an amount sufficient to effect beneficial or desired results. An effective amount can be administered in one or more administrations. For purposes of this invention, an effective amount of a cytoprotective composition is an amount that is sufficient to ameliorate, stabilize, reverse, slow or delay the progression of injury(ies) in mammalian subjects i) at risk for a disease, disorder or condition associated with inflammation, or ii) associated with, due to and/or symptoms of inflammation. Preferably, amelioration of symptoms due to inflammation can be quantified by an assay measuring, for example, reduction in CRP levels and/or reduction in inflammatory markers, such as by measuring reduction in cytokines such as, but not limited to interleukins 1–17 (IL 1–17) associated with inflammation; and TNF-α. Other assays are disclosed herein. For example, in Example 1A disclosed herein, gamma-tocopherol, beta-tocopherol and delta-tocopherol were shown to be effective at reducing CRP levels. Amelioration is at least about 30%, at least about 50%, at least about 70%, at least about 80%, and at least about 90% reduction in the levels of inflammatory markers associated with inflammation or an inflammatory condition or a reduction in the symptoms associated with inflammation such as for example, pain and/or edema associated with inflammation.

A "mammalian subject" or "individual" (used interchageable herein) includes, but is not limited to, a human, a farm animal, a sport animal, and a pet.

By "amelioration" is meant the prevention, reduction or palliation of a state, or improvement of the state of a subject; the amelioration of a stress is the counter-acting of the negative aspects of a stress. Amelioration includes, but does not require complete recovery or complete prevention of a stress.

By "treatment" or "treating" is meant any treatment of a disease or disorder, in a mammal, including: preventing or protecting against the disease or disorder, that is, causing, the clinical symptoms of the disease not to develop; inhibiting the disease, that is, arresting or suppressing the development of clinical symptoms; and/or relieving the disease, that is, causing the regression of clinical symptoms.

"As used herein, the term "comprising" and its cognates are used in their inclusive sense; that is, equivalent to the term "including" and its corresponding cognates.

General Methods

General techniques for chemical manipulations are known in the art and are generally described in, for example, Haugland (1996) *Handbook of Fluorescent Probes and Research Chemicals*, Sixth Edition, Molecular Probes, Inc.; Carruthers (1986) *Some Modern Methods of Organic Synthesis*, Third Edition, Cambridge University Press; and Warren (1978) *Designing Organic Syntheses*, John Wiley & Sons, Ltd. Molecular biology techniques are generally described in, for example, Sambrook et al. (1989), *Molecular Cloning: A Laboratory Manual*, Second Edition; and Ausubel et al., eds. (1987) *Current Protocols In Molecular Biology*. Reagents useful in applying these techniques are widely known in the art and commercially available from a number of vendors.

Inflammatory Markers

A number of proximal mediators of the inflammatory response have been identified and include the inflammatory cytokines, interleukin-1β (IL-1β) (U.S. Pat. No. 6,210,877) and tumor necrosis factor alpha (TNF-α), as described in U.S. Pat. Nos. 5,993,811 6,210,877 and 6,203,997. Other molecules have been reported for use as markers of systemic inflammation, including for example, CRP (Ridker et al. 2000 *N. E. J. M.* 342(12):836–43; Spanheimer supra); certain cellular adhesion molecules such as sICAM-1 (U.S. Pat. No. 6,049,147); and B61 (U.S. Pat. No. 5,688,656). Other proteins associated with inflammation include leukotriene, thromboxane, and isoprostane. Other proteins or markers associated with inflammation include serum amyloid A protein, fibrinectin, fibrinogen, leptin, prostaglandin E2, serum procalcitonin, soluble TNF receptor 2, and elevated white blood count, including percent and total granulocytes (polymorphonuclear leukocytes)m monocytes, lymphocytes and eosinophils.

C-reactive protein (CRP) is an acute phase protein in humans that increases rapidly in concentration as a result of systemic inflammation, for example, as a result of tissue injury, inflammation or infection and in IDDM patients without macrovascular disease. As used herein, "elevated level(s) of CRP" refer to CRP levels being elevated with respect to an individual's baseline CRP levels. Generally speaking, the normal range of CRP in human serum is 0.08–2 milligram (mg) per liter. CRP levels can increase between 100–1000-fold during an inflammatory response. Elevated serum levels of CRP are seen 6–12 hours after an inflammatory stimulus, and maximum levels are reached within 48–72 hours. Generally, CRP levels will return to normal 55–10 days after remission of inflammation. Because the accumulation of CRP in serum closely parallels the course of inflammation and tissue injury, CRP has been used as a diagnostic tool to detect inflammation and to monitor the clinical course of a number of diseases. For example, CRP levels are found to exceed 50 mg/l in rheumatoid arthritis, systemic lupus erythematosus (SLE), ulcerative colitis, Crohn's disease, acute pancreatitis, cardiac infarction, septicemia, bacterial meningitis, and pneumonia. Further, CRP levels have been correlated with increased risk of cardiovascular disease and stroke (Lagrand, W. K., et al, *Circulation* 100: 96–102, 1999). CRP levels are also elevated during inflammatory disorders such as infection, trauma, surgery, tissue infarction, and in IDDM patients without macrovascular disease. The magnitude of the increase varies from about 50% to as much as 100-fold during systemic inflammation (Gabay, C., et al., *New Engl. J. Med.* 340: 448–454, 1999). Most CRP is produced in hepatocytes in response to pro-inflammatory cytokines, especially interleukin-6 and 1β (Ganter, U., et al., *EMBO J.* 8: 3773–3779, 1989), although macrophages have also been reported to release CRP (Dong, Q, et al, *J. Immunol.* 156: 481504820, 1996).

Elevated CRP levels have been reported in a number of inflammatory conditions, including, but not limited to insulin-dependent diabetes mellitus (IDDM; Type I; (Schalkwijk, C G., et al., 1999, *Diabetologia* 42(3): 351–7), non-insulin-dependent diabetes mellitus (NIDDM; Type II), metabolic syndrome, cardiovascular disease, atrial fibrillation (Chung M. K, et al, 2001, *Circulation* 104(24): 2886–91), paroxysmal atrial fibrillation (Dernellis, J., et al., 2001, *Acta Cardiologica* 56(6): 375–80), cardiac allograft vasculopathy (CAVD; in heart transplant patients) Pethig, K., et al., 2000, *Circulation* 102: 111233–6), mastitis (WO 9522767), pre-eclampsia, peripheral artery disease, inflammatory bowel disorders (e.g., Crohn's disease; Poullis, A. P., et al., *Eur J. Gastro Hepat* 14(4):409–412 (2002), stroke, tissue infarction, Lumbosciatic syndrome (local nerve root impingement) (Le Gars, L, et al., 2001, *Bone, Joint, Spine: Revue du Rhumatisme* 67(5): 452–5), uremic patients having end-stage renal disease (ESRD), or inflammation-associated conditions such as infection (bacterial, viral, and protozoal), bacterial meningitis (Shimetani, N, et al., 2001, *Scan. J. Clin Lab. Invest.* 61(7): 567–74), trauma, surgery, sepsis (Tschaikowsky, K., et al., 2002, *Critical Care Med.* 30(5): 1015–23), biomaterial implants (Lobler, M., et al., *J. Biomaterials Research* 61(1);165–167), smoking, obesity, premenstrual syndrome, rheumatoid arthritis, aging. Women taking hormone replacement therapy (estrogen+progestin; HRT) were also found to have elevated CRT and increased risk of cardiovascular events (Ridker, P M, et al, 1999, *Circulation* 100: 713–716; Hulley, S., et al., 1998, *JAMA* 280: 605–613).

Other inflammatory conditions associated with increased CRP levels include acute allergic reactions (Lin, R. Y., et al, 2001, *Ann Allergy Asth Immunol* 87(5): 412–16), respiratory conditions, such as asthma (Yamaguchi, A., et al., 2000, *J. Clin. Pharmacol.* 40(3): 284–9), COPD (Malo, O, et al., 2002, *Arch Bronconeumol* 38(4):172–6), or the like, periodontal disease, such as gingivitis (Glurich, I., et al., 2002, *Clin. Diag. Lab. Immunol.* 9(2): 425–32; Noack, B., et al., 2001, J. Periodontology, 72(9): 1221–7).

Recent studies have shown that mortality in patients having coronary artery disease can be correlated with high levels of CRP (Bickel, C., et al., 2002, *Am. J. Cardiology* 89(8):901–908, 2002; Jialal, I. and Devaraj, S. *Am. J. Clin Path* 116 Suppl: S108–15, 2001). In a large prospective study, patients with unstable angina and elevated C-reactive protein levels had a 3-fold higher risk of coronary events during a 90-day follow-up. (Ferreiros, et al, 1999, *Circulation* 99: 237–42). Similarly, elevated levels of IL-1 and IL-6 have been shown to be associated with aneurysm associated with unstable angina (Biasucci, L. M., 1999, *Circulation* 99: 2079–2084). Further, elevated CRP levels were associated with a doubling of risk of ischemic stroke in hypertensive patients (DiNapoli, M., et al., 2001, *Stroke* 32: 133–138) and with increased risk of developing age-related cataracts (Schaumberg, D. A., et al., 1999, *Ann. Epidemiol* 9: 166–171).

Likewise, in uremic patients (having ESRD), elevated CRP and IL6 levels may contribute to enhanced CV morbidity and mortality. Elevated CRP levels are also associated with Type II diabetes, obesity and may also be predictive of mortality in these conditions.

Cytokines are intercellular mediators secreted by the lymphocytes and/or macrophages. Cytokines play a role in the generation of an immune response, such as in an immune response to an infection or infectious organism. Cytokines including, for example, interferons, e.g., IFN-alpha, and TNFs induce other cytokines which participate in the development of different autoimmune conditions and diseases. U.S. Pat. No. 6,333,032 teaches that neutralizing certain key cytokines (IFN-alpha, IFN-gamma and TNF), results in the decrease, halt of or prevents the synthesis of downstream cytokines induced by them. Furthermore, in certain autoimmune conditions or diseases, including IDDM and SLE, the induction of another cytokine (interleukins, specifically IL-6) is also significant IL-6 is made by several cells, including T-cells, B-cells, and others (Hirano et al., *Clin. Immunol.* 62:S60 (1992)), and induces insulinitis in IDDM. In response to IFN-gamma and TNF, B-cells of the pancreas produce large quantities of IL-6. It is also an important pathological factor in the pathogenesis of SLE, where is has been found to be present at a high level. IL-6 stimulates differentiation in B-cells and hyperactivity of T-cells (Snick et al., *Ann. Rev. Immunol.* 8:253 (1990)). The increase in IL-6 parallels the increase of TNF-alpha (Majer et al., *Lupus* 2:359–365 (1993)).

In some examples, the present invention provides non-alpha-tocopherol enriched tocopherol compositions and non-alpha-tocopherol metabolite enriched compositions in particular for use in reducing inflammatory markers, in particular CRP, associated with inflammation and/or inflammatory conditions including cardiovascular diseases or disorders, including atrial fibrillation, unstable angina, coronary artery disease, peripheral artery disease, cardiac allograft vasculopathy (CAVD); mastitis; preclampsia; inflammatory bowel conditions; stroke; tissue infarction; lumbosciatic; estrogen/progestin hormone replacement therapy (HRT); infection (bacterial, viral and protozoan); bacterial meningitis; trauma; surgery; biomaterial implants; smoking; obesity; neurodegenerative diseases such as, Alzheimers; infectious disease, such as, for example, myocarditis, cardiomyopathy, acute endocarditis, pericarditis; atherosclerosis; Systemic Inflammatory Response Syndrome (SIRS)/sepsis; adult respiratory distress syndrome (ARDS); asthma; rheumatoid arthritis, osteoarthritis, systemic lupus erythematosis; Airway hyper-responsiveness (AHR); bronchial hyper-reactivity; Chronic Obstructive Pulmonary disease (COPD); Congestive Heart Failure (CHF); inflammatory complications of diabetes mellitus type I and type II; metabolic syndrome; end stage renal disease (ESRD), pre-menstrual syndrome (PMS) or muscle fatigue or inflammation; multiple organ dysfunction syndrome (MODS); airway hyper-responsiveness (AHR); bronchial hyper-reactivity; aging; acute allergic reactions; periodontal disease, such as gingivitis, and dermal conditions including inflammatory skin conditions.

In some examples of the present invention, a gamma-tocopherol enriched tocopherol composition and/or a gamma-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; and periodontal disease.

In some examples of the present invention, a beta-tocopherol enriched tocopherol composition and/or a beta-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; periodontal disease and inflammatory skin conditions.

In other examples of the present invention, a delta-tocopherol enriched tocopherol composition and/or a delta-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; periodontal disease and non-psoriatic inflammatory skin conditions.

Inflammatory Conditions

Myocarditis and cardiomyopathy are a group of diseases primarily of the myocardium which do not result from hypertensive, congenital, ischemic, or valvular heart disease. Myocarditis generally defines acute myocardial disease characterized by inflammation, and cardiomyopathy defines more chronic myocardial diseases in which the inflammatory features are not conspicuous. Myocarditis and cardiomyopathy can lead to fever, chest pain, leukocytosis, increased erythrocyte sedimentation rate, left ventricular failure, arrythmias, heart block, ECG changes, and eventually cardiac failure. See U.S. Pat. No. 5,496,832.

Myocarditis and cardiomyopathy result from an immune response against the myocardium, including lymphocytic infiltration and inflammation. The immune response can occur secondary to infectious diseases such as Chagas' disease (American trypanosomiasis), toxoplasmosis, trichinosis, ricksettal infection (typhus, Rocky Mountain spotted fever), fungal infections, and metazoan parasites; or secondary to autoimmune diseases such as rheumatic fever, rheumatoid arthritis, systemic lupus erythematosus, progressive systemic sclerosis, and polyarteritis nodosa. The immune response leading to myocarditis can be idiopathic in nature as seen in Fiedler's myocarditis. Additionally, myocarditis can be caused by drug reaction to penicillin or sulfonamide, for example. See U.S. Pat. No. 5,496,832.

Acute pericarditis is defined as an inflammatory disease of the visceral or parietal pericardium and can occur secondary to bacterial, viral (especially echovirus, and Coxsackie Group B), or fungal infection, and can accompany systemic diseases such as rheumatoid arthritis, systemic lupus erythematosus, scleroderma, and uremia. Pericarditis can also occur after cardiac trauma or cardiac surgery that is suggested as being caused by immunologic hypersensitivity. Acute pericarditis can lead to chronic constrictive pericarditis, pericardial tamponade, effusion, and hemorrhage, all of which can result in cardiac failure. See U.S. Pat. No. 5,496,832.

Inflammation, particularly macrophage-mediated and chronic inflammation, has been cited as central to atherosclerosis (U.S. Pat. Nos. 5,877,203 6,210,877) and may serve as a prognostic marker for heightened risk of myocardial infarction (Boisvert et al. 1998 *J. Clin. Invest.* 101(2):353–363). Atherosclerosis (also known as arteriosclerosis) is the term used to described progressive luminal narrowing and hardening of the arteries. This disease process can occur in any of the arteries in the body leading to a variety of conditions including stroke (hardening or narrowing of arteries leading to the brain), gangrene (hardening or narrowing of peripheral arteries) and CAD (hardening or narrowing of arteries supplying the myocardium). CAD can in turn lead to myocardial ischemia or myocardial infarction. Cardiovascular disorders associated with atherosclerotic disease (and therefore inflammation) can include, for example, myocardial infarction, stroke, angina pectoris and peripheral arteriovascular disease. Macrovascular complications, including atherosclerosis and related conditions are often complications associated with diabetes.

Luminal narrowing of the arteries is the result of the depositions of atheromatous plaque. The plaque consists of a mixture of inflammatory and immune cells, fibrous tissue and fatty material such as low density lipids (LDLs), modifications thereof and α-lipoprotein. The initial causes of atherosclerosis are not completely understood, but it has been suggested that the pathogenesis may include the following stages: endothelial cell dysfunction and/or injury; monocyte recruitment and macrophage formation; lipid deposition and modification; vascular smooth muscle cell proliferation; and synthesis of extracellular matrix.

Trauma or infection may result in acute life-threatening conditions which include systemic inflammatory response syndrome (SIRS), or adult respiratory distress syndrome (ARDS). When SIRS is caused by infection, it is termed sepsis, which in turn has progressively severe stages (severe sepsis and septic shock). SIRS/sepsis may also result from numerous sources, including bacterial, viral, parasitic, rickettsial or fungal infection, and/or SIRS resulting from non-infectious causes such as burns, pancreatitis, multitrauma, severe surgical trauma, transplant rejection, marked autoimmune rejection, ischemia reperfusion, transfusion reaction or heat stroke. The marked augmentation of pro-inflammatory cytokines which leads to SIRS may also lead to multiple organ dysfunction syndrome (MODS) (e.g. varying degrees of fever, hypoxemia, tachypnea, tachycardia, endothelial inflammation, myocardial insufficiency, hypoperfusion, altered mental status, vascular collapse, which may lead to ARDS, coagulopathy, cardiac failure, renal failure, shock and/or coma).

Depending on the severity of SIRS/sepsis, the mortality rate averages 20–70% (U.S. Pat. No. 5,992,811). Additionally, in the United States, almost one-half million cases occur yearly, with SIRS/sepsis estimated to be the 13th leading cause of death and the major proximate cause of mortality in intensive care units (Centers for Disease Control, *MMWR*, 1990L 39:31; Lowry et al., 1994 *Crit, Care Med.* 22:S1–2).

Chronic asthma can be considered to be predominantly an inflammatory disease with associated bronchospasm. The degree of reactivity and narrowing of the bronchi in response to stimuli is greater in asthmatics than in normal individuals. Persistent inflammation is responsible for the bronchial hyperreactivity or airway hyperresponsiveness (AHR). Mucosal edema, mucus plugging and hypersecretion may also be present and pulmonary parenchyma is normal. Airway narrowing may reverse spontaneously or through treatment. Type 1 (immediate) immune responses may play an important role in the development of asthma in children and many adults; however, when onset of disease occurs in adulthood, allergic factors may be difficult to identify. Exposure to cold dry air, exercise and other aggravating factors may also trigger asthma.

Bronchial hyperreactivity (or airway hyperreactivity, AHR) is a hallmark of asthma and is closely related to underlying airway inflammation. Worsening of asthma and airway inflammation is associated with increase in bronchial hyperreactivity, which can be induced by both antigenic and non-antigenic stimuli. Beta$_2$-adrenergic agonists are potent agents for the treatment of bronchospasm, but have no effect on airway inflammation or bronchial hyperreactivity. In fact, chronic use of beta$_2$-adrenergic agents alone, by causing down regulation of beta$_2$-receptors, may worsen bronchial hyperreactivity. At present, corticosteroids are the one of the most effective agents available which diminish bronchial hyperreactivity. Although inhaled corticosteroids are relatively safe in adult patients with asthma, these agents have tremendous toxicity in children, including adrenal suppression and reduced bone density and growth.

While asthma was once thought of as a disease associated primarily with morbidity, it is now being recognized that asthma is more often associated with mortality than generally thought. In the United States, the annual mortality for asthma, among persons 5 to 34 years is 0.4 per 100,000 people. Deaths are most likely the result of asphyxiation caused by inadequately treated airflow obstruction and generally occur outside of the hospital (Leatherman et al., 1992 Ch. 14(II) in *Scientific American Medicine* Rubenstein, E. and Federman, D. D. eds. Scientific American, Inc., New York).

Inflammation is also associated with pulmonary or respiratory conditions other than asthma, including adult respiratory distress syndrome (ARDS), an acute and life threatening disease which can lead to multiple organ dysfunction (MOD) (U.S. Pat. No. 5,780,237), and chronic obstructive pulmonary disease (COPD) which is often a complication of cystic fibrosis (Kennedy 2001 *Pharmacotherapy* 215:593–603). ARDS is a classic example of a restrictive diffuse pulmonary disease while COPD and asthma are exemplary of an obstructive (or airway) disease. Obstructive diseases are characterized by an increase in resistance to air flow due to partial or complete obstruction, while restrictive diseases are characterized by reduced expansion of lung parenchyma and a decreased total lung capacity. COPD (also known as COAD, chronic obstructive airway disease) refers to a group of conditions, emphysema, chronic bronchitis, bronchial asthma and bronchiectasis, which are accompanied by chronic or recurrent obstruction to air flow within the lung (Cotran et al., "Robbins Pathologic Basis of Disease" 4th Ed. 1989, W.B. Saunders Co., Philadelphia, Pa.).

ARDS (also known as acute respiratory distress syndrome) is defined as respiratory failure in adults or children that results from diffuse injury to the endothelium of the lung (as in sepsis, chest trauma, massive blood transfusion, aspiration of the gastric contents, or diffuse pneumonia) and is characterized by pulmonary edema, respiratory distress and hypoxemia (Merriam-Webster's Medical Desk Dictionary 1996 Merriam-Webster, Inc. Springfield, Mass.). ARDS can be due to either trauma or infection and generally occurs in a clinical setting. CF pulmonary disease is characterized as multi-factorial, involving a cycle of airway obstruction, chronic infection and excessive local inflammation that leads to development of bronchiectasis (Kennedy supra), which can be a chronic inflammatory or degenerative condition of the bronchi or bronchioles. Uncontrolled, chronic inflammation directly damages the airway wall, which leads to bronchiectasis and decline in pulmonary function.

Diabetes mellitus is a chronic disorder affecting carbohydrate, fat and protein metabolism. The long term complications of diabetes include numerous vascular conditions, macrovascular, microvascular, and neurologic. There are a number of types of diabetes, including insulin-dependent diabetes mellitus (IDDM, also known as insulin-sensitive diabetes, type I or juvenile diabetes), non-insulin-dependent diabetes mellitus (NIDDM, also known as insulin-insensitive-dependent diabetes, type II, adult-onset or late-onset diabetes), secondary diabetes and gestational diabetes. IDDM is characterized by absolute insulin deficiency associated with atrophy of the islets of the pancreas, whereas NIDDM patients have nearly normal islet mass, but do not secrete sufficient insulin to meet the increased demand due to insulin resistance. Secondary diabetes is associated with other conditions, including pancreatic disease (e.g. chronic pancreatitis), endocrine diseases (e.g. acromegaly or Cushing's disease), and certain medications or toxins (e.g. thiazides, glucocorticoids). Polycystic ovary syndrome is also associated with elevated insulin levels, insulin resistance or diabetes.

Gestational diabetes includes glucose intolerance with the onset of pregnancy, usually at 24–30 weeks gestation (Nathan 1993 Ch. 9(IV) in *Scientific American Medicine* Rubenstein & Federman, eds., Scientific American, Inc., New York). Certain individuals may also suffer from impaired glucose tolerance, which is asymptomatic, but one third of those with the condition eventually develop NIDDM.

While the etiology and ultimate causes of diabetes mellitus vary, the complications linked to the associated metabolic dysfunction and the complications which arise therefrom are common to all types. Common complications include microvascular, neurologic and macrovascular conditions. Complications such as retinopathy and nephropathy are specific for diabetes. Nephropathy associated with diabetes may lead to pre-end stage renal disease (ESRD) and ESRD.

It has been reported (Spanheimer, 2001, *Postgrad. Med.* 109(4) 26) that diabetes may lead to a chronic, low-grade inflammatory state possibly caused by glycosylation of proteins that activate macrophages or by increased oxidative stress. A marker for systemic inflammation is C-reactive protein (CRP). See U.S. Pat. No. 6,040,147. In humans CRP levels are elevated during inflammatory disorders such as infection, trauma, surgery, tissue infarction, and in IDDM patients without macrovascular disease. The magnitude of the increase varies from about 50% to as much as 100-fold during systemic inflammation (Gabay, C., et al., *New Engl. J. Med.* 340: 448–454, 1999). Recent evidence has shown that CRP is also a risk factor for cardiovascular disease and stroke where inflammation plays an important role (Lagrand, W. K., et al, *Circulation* 100: 96–102, 1999). Most CRP production is from hepatocytes in response to pro-inflammatory cytokines, especially interleukin-6 and $1\beta$ (Ganter, U., et al., *EMBO J.* 8: 3773–3779, 1989), although macrophages have also been reported to release CRP (Dong, Q, et al, *J. Immunol.* 156: 481504820, 1996).

These findings have led researchers to suggest that inflammation may precede atherosclerosis in diabetics and that CRP may serve as a marker for tracking the condition (Spanheimer supra; Ridker et al. 2001 *N. E. J. M.* 344(26): 1959–1965).

The term pre-menstrual syndrome (PMS, also referred to as pre-menstrual tension, PMT), encompasses a wide variety of physical and mental symptoms which are associated with the female menstrual cycle and occur cyclically. Symptoms usually peak during the late luteal phase (i.e. after ovulation) of a woman's cycle and abate with the beginning of menstrual blood loss. The severity of symptoms associated with PMS range from mild to incapacitating and it has been estimated that up to 90% of women who menstruate suffer from some degree of PMS, while 20–40% suffer symptoms severe enough to lead to physical or mental incapacitation (U.S. Pat. No. 6,174,542). The severity of symptoms can vary from month to month or year to year for a particular woman. It has been estimated that the cost of lost work due to PMS in the United States exceeds ten billion dollar annually (U.S. Pat. No. 4,945,103). Nitric oxide production is induced by exogenous or endogenous inflammatory stimuli (U.S. Pat. No. 5,629,322) and has been implicated in the pathology associated with a number of conditions. Current treatments for the symptoms of PMS include the administration of anti-inflammatory drugs, particularly non-steroidal anti-inflammatory drugs (NSAIDs) such as ibuprofen, naproxen, the administration of antihistamines, diuretics, psychoactive drugs such as lithium carbonate and benzodiazepines, as well as SSRIs, such as Prozac®.

Furthermore, the role of inflammatory cytokines (and to some extent CRP) is well recognized for the progression of joint destruction, such as in rheumatoid arthritis and osteoarthritis. Inflammatory cytokines (IL-1, IL-6 and TNF-$\alpha$) are also known to increase bone resorption in disorders such as osteoporosis.

Compositions

Provided herein are non-alpha-tocopherol enriched tocopherol compositions. Examples of non-alpha-tocopherol enriched tocopherol compositions include: gamma-tocopherol enriched tocopherol compositions comprising gamma-tocopherol which may further comprise a gamma-tocopherol metabolite(s), and/or other tocopherols, e.g., alpha-, delta-, and/or beta-tocopherol, for use in reducing the level of an inflammatory marker, in particular, CRP, associated with an inflammatory conditions and for use as cytoprotectants against damage, injury(ies) and/or a symptom associated with inflammation; beta-tocopherol enriched tocopherol compositions comprising beta-tocopherol which may further comprise a beta-tocopherol metabolite(s), and/or other tocopherols, e.g., alpha-, delta-, and/or gamma-tocopherol, for use in reducing the level of an inflammatory marker, in particular, CRP, associated with an inflammatory conditions and for use as cytoprotectants against damage, injury(ies) and/or a symptom associated with inflammation; and delta-tocopherol enriched tocopherol compositions comprising delta-tocopherol which may further comprise a delta-tocopherol metabolite(s), and/or other tocopherols, e.g., alpha-, gamma-, and/or beta-tocopherol, for use in reducing the level of an inflammatory marker, in particular, CRP, associated with an inflammatory conditions and for use as cytoprotectants against damage, injury(ies) and/or a symptom associated with inflammation.

The present invention provides methods of treating and/or ameliorating symptoms associated with non-cardiovascular inflammation in a mammalian subject, comprising administering to the subject a gamma-tocopherol enriched tocopherol composition in a pharmaceutically effective amount, and by said administering, reducing symptoms associated with said inflammation.

The present invention also provides methods of treating and/or ameliorating symptoms associated with non-cardiovascular inflammation in a mammalian subject, comprising administering to the subject a gamma-tocopherol metabolite enriched composition in a pharmaceutically effective amount, and by said administering, reducing symptoms associated with said inflammation. In preferred embodiments, the gamma-tocopherol metabolite is 2,7,8-trimethyl-2-(2'-carboxyethyl)-6-hydroxychroman (gamma-CEHC).

The present invention provides methods of treating and/or ameliorating symptoms associated with inflammation in a mammalian subject, comprising administering to the subject a beta-tocopherol enriched tocopherol composition in a pharmaceutically effective amount, and by said administering, reducing symptoms associated with said inflammation.

The present invention also provides methods of treating and/or ameliorating symptoms associated with inflammation in a mammalian subject, comprising administering to the subject a beta-tocopherol metabolite enriched composition in a pharmaceutically effective amount, and by said administering, reducing symptoms associated with said inflammation. In preferred embodiments, the beta-tocopherol metabolite is 2,5,8-trimethyl-2-(2-carboxyethyl)-6-hydroxychroman (beta-CEHC).

The present invention provides methods of treating and/or ameliorating symptoms associated with inflammation in a mammalian subject, comprising administering to the subject a delta-tocopherol enriched tocopherol composition in a pharmaceutically effective amount, and by said administering, reducing symptoms associated with said inflammation, wherein said administration specifically excludes topical administration of delta-tocopherol enriched tocopherol compositions for the treatment of psoriasis as described in U.S. Pat. No. 4,325,965; but does encompasses systemic administration of delta-tocopherol enriched tocopherol compositions for the treatment of psoriasis; and does encompasses topical administration of delta-tocopherol enriched tocopherol compositions for non-psoriatic dermal conditions, diseases or disorders.

The present invention also provides methods of treating and/or ameliorating symptoms associated with inflammation in a mammalian subject, comprising administering to the subject a delta-tocopherol metabolite enriched composition in a pharmaceutically effective amount, and by said administering, reducing symptoms associated with said inflammation. In preferred embodiments, the delta-tocopherol metabolite is 2,8,-dimethyl-2-(2-carboxyethyl)-6-hydroxychroman (delta-CEHC).

The present invention also provides methods for reducing the levels of inflammatory markers and proteins associated with inflammation, such as for example, CRP; cytokines associated with inflammation, including IL-1 through 17; TNF-$\alpha$; and B61; and methods of reducing pain associated with inflammation and/or reducing edema associated with inflammation.

In some embodiments, the non-alpha-tocopherol enriched tocopherol compositions of the present invention comprise at least 50% non-alpha-tocopherol, at least 55% non-alpha-tocopherol, at least 60% non-alpha -tocopherol, at least 65% non-alpha -tocopherol, at least 70% non-alpha -tocopherol, at least 75% non-alpha-tocopherol, at least 80% non-alpha-tocopherol, at least 85% non-alpha-tocopherol, at least 90% non-alpha-tocopherol and at least 95% non-alpha-tocopherol. Non-alpha-tocopherol enriched tocopherol compositions comprise less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, non-alpha-tocopherol enriched tocopherol compositions consist essentially of the non-alpha-tocopherol as the active ingredient. As used herein, an "active ingredient" is one that is able to reduce the level of a marker of inflammation, such as for example, CRP and/or treat or ameliorate the symptoms of inflammation in a mammalian subject.

The present invention provides non-alpha-tocopherol metabolite enriched compositions and methods for using such compositions. In some embodiments, the non-alpha-tocopherol metabolite enriched compositions of the present invention comprise at least 50% non-alpha-tocopherol metabolite, at least 55% non-alpha-tocopherol metabolite, at least 60% non-alpha-tocopherol metabolite, at least 65% non-alpha-tocopherol metabolite, at least 70% non-alpha-tocopherol metabolite, at least 75% non-alpha-tocopherol metabolite, at least 80% non-alpha-tocopherol metabolite, at least 85% non-alpha-tocopherol metabolite, at least 90% non-alpha-tocopherol metabolite and at least 95% non-alpha-tocopherol metabolite. Non-alpha-tocopherol metabolite enriched compositions comprise less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, non-alpha-tocopherol metabolite enriched compositions consist essentially of non-alpha-tocopherol metabolite as the active ingredient.

In some embodiments, a non-alpha-tocopherol enriched tocopherol composition or a non-alpha-tocopherol metabolite composition is able to reduce inflammation at least about 30%, at least about 40%, at least about 50%, at least about 60%, at least about 70%, at least about 80%, at least about 90%, or at least about 95%, as measured by a reduction in the levels of inflammatory markers associated with inflammation, such as for example, CRP and cytokines associated with inflammation; or as measured by a reduction in the symptoms associated with inflammation such as for example, pain and/or edema associated with inflammation; or as measured in assays and experimental models disclosed herein.

In additional embodiments, a gamma-tocopherol enriched tocopherol composition comprises gamma-tocopherol in an amount effective to reduce inflammation, such as measured by a reduction in the levels of inflammatory markers associated with inflammation, such as for example, CRP and/or cytokines associated with inflammation and may further comprise a gamma-tocopherol metabolite and may further comprise alpha-tocopherol, delta-tocopherol and/or beta-tocopherol, or other ingredients. In further embodiments, a gamma-tocopherol metabolite enriched composition comprises a gamma-tocopherol metabolite in an amount effective to reduce inflammation such as measured by a reduction in the levels of inflammatory markers associated with inflammation, such as for example, CRP and/or cytokines associated with inflammation and may further comprise gamma-tocopherol and may further comprise alpha-tocopherol, delta-tocopherol and/or beta-tocopherol, or other ingredients.

In additional embodiments, a beta-tocopherol enriched tocopherol composition comprises beta-tocopherol in an amount effective to reduce inflammation such as measured by a reduction in the levels of inflammatory markers associated with inflammation, such as for example, CRP and/or cytokines associated with inflammation and may further comprise a beta-tocopherol metabolite and may further comprise alpha-tocopherol, delta-tocopherol and/or gamma-tocopherol, or other ingredients. In further embodiments, a beta-tocopherol metabolite enriched composition comprises a beta-tocopherol metabolite in an amount effective to reduce inflammation such as measured by a reduction in the levels of inflammatory markers associated with inflammation, such as for example, CRP and/or cytokines associated with inflammation and may further comprise beta-tocopherol and may further comprise alpha-tocopherol, delta-tocopherol and/or gamma-tocopherol, or other ingredients.

In additional embodiments, a delta-tocopherol enriched tocopherol composition comprises delta-tocopherol in an amount effective to reduce inflammation such as measured by a reduction in the levels of inflammatory markers associated with inflammation, such as for example, CRP and/or cytokines associated with inflammation and may further comprise a delta-tocopherol metabolite and may further comprise alpha-tocopherol, beta-tocopherol and/or gamma-tocopherol, or other ingredients. In further embodiments, a delta-tocopherol metabolite enriched composition comprises a delta-tocopherol metabolite in an amount effective to reduce inflammation such as measured by a reduction in the levels of inflammatory markers associated with inflammation, such as for example, CRP and/or cytokines associated with inflammation and may further comprise delta-tocopherol and may further comprise alpha-tocopherol, beta-tocopherol and/or gamma-tocopherol, or other ingredients.

Assays for measuring the effect of non-alpha-tocopherol enriched tocopherol compositions and non-alpha-tocopherol metabolite enriched compositions are provided herein and are known to those of skill in the art.

In a CRP assay, such as the one disclosed herein, gamma-, beta-, and delta-tocopherol were effective at reducing CRP production in human Hep3B cells stimulated with IL-1B, IL-6 and dexamethasone.

Tocopherols are chemical entities which, in general, contain a 6-chromanol ring structure and a side chain at the 2-position. Prototypical tocopherols include alpha-, beta-, delta- and gamma-tocopherol. Non-alpha-tocopherols include gamma-, beta-, and delta-tocopherol. The tocopherols have the general formula:

Tocopherols:

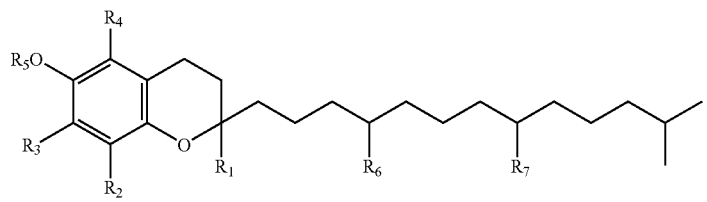

|       | R2  | R3  | R4  |
|-------|-----|-----|-----|
| Alpha | CH3 | CH3 | CH3 |
| Gamma | CH3 | CH3 | H   |
| Beta  | CH3 | H   | CH3 |
| Delta | CH3 | H   | H   |

R1 = CH3 with S or R configuration
R6 = CH3 with S or R configuration
R7 = CH3 with S or R configuration
R5 = H or CH3 or acetate or succinate Gamma-tocopherol, beta-tocopherol, and delta-tocopherol have the structure as shown in Brigelius-Flohe, et al., 1999, *The FASEB Journal, vol.* 13: 1145.

In preferred embodiments of the present invention, non-alpha-tocopherol enriched tocopherol compositions include for example:

non-alpha-tocopherol enriched composition comprising greater than 90% non-alpha-tocopherol or greater than 95% non-alpha-tocopherol;

non-alpha-tocopherol metabolite enriched composition comprising greater than 90% non-alpha-tocopherol metabolite or greater than 95% non-alpha-tocopherol metabolite; and non-alpha-tocopherol enriched composition comprising a non-alpha-tocopherol metabolite.

In an example described herein, a non-alpha-tocopherol enriched tocopherol composition comprising at least 60% gamma-tocopherol and at least 28% delta-tocopherol, when administered to individuals with ESRD, was able to reduce CRP and IL-6 levels in the serum samples of the individuals.

Activity of a non-alpha-tocopherol enriched tocopherol composition or a non-alpha-tocopherol metabolite enriched composition can be experimentally tested, for example, in an assay which measures the level of an inflammatory marker associated with inflammation. Such assays are detailed in Examples and are known to those of skill in the art.

Specific Markers and Assays for Inflammation

A number of proximal mediators of the inflammatory response have been identified and include the inflammatory cytokines, interleukin-1β (IL-1β) (U.S. Pat. No. 6,210,877) and tumor necrosis factor alpha (TNF-α), as described in U.S. Pat. Nos. 5,993,811 6,210,877 and 6,203,997. Other molecules have been reported for use as markers of systemic inflammation, including for example, CRP (Ridker et al. 2000 *N. E. J. M.* 342(12):836–43; Spanheimer supra); certain cellular adhesion molecules such as sICAM-1 (U.S. Pat. No. 6,049,147); and B61 (U.S. Pat. No. 5,688,656). Other proteins associated with inflammation include leukotriene, thromboxane, and isoprostane.

There presently are commercial sources which produce reagents for assays for C-reactive protein, for example, but not limited to, CalBiochem (San Diego, Calif.). B61 is secreted by endothelial cells, fibroblasts and keratinocytes in response to lipopolysaccharide and the pro-inflammatory cytokines IL-1 and TNF. The B61 gene product is not, however, induced in response to other agents such as growth factors and interferon, thus induction of B61 is thus highly specific to inflammation (U.S. Pat. No. 5,688,656). The presence of B61 transcript can be detected directly by in situ hybridization using probes of encoding cDNA. Alternatively, the B61 protein can be measured in biological fluids such as plasma, cerebrospinal fluid or urine using an antibody-based assay. These assay procedures known in the art and described in particular in U.S. Pat. No. 5,688,656 are useful in both prognostic and diagnostic applications.

In studies carried out in support of the present invention, a combination of Interleukin-1β, IL-6, and dexamethasone is used to induce CRP production, and counter-agents are tested for their ability to reduce this production in cultured liver cells, as detailed in Example 1A. The assay is performed on cells grown in 96-well format allowing high throughput screening of compounds. As described herein, gamma-tocopherol, beta-tocopherol and delta-tocopherol were able to reduce CRP levels in an assay such as the one described in Example 1A.

Another useful cell screening assay, exemplified herein in Example 1B, is the E-selectin (ELAM) production assay, which measures activity of test compounds in reducing expression of ELAM in activated endothelial cells. Briefly, endothelial cells are activated by adding known activators such as lipopolysaccharide, TNF, or IL-1β, alone or in some combination. Activated cells produce ELAM, which can be measured using, for example, an E-selectin monoclonal antibody-based ELISA assay. In studies carried out in support of the present invention, ELAM production was decreased by gamma-tocopherol, beta-tocopherol, and delta-tocopherol but not by alpha-tocopherol. The present invention encompasses mixtures of tocopherols, such as for example, the composition described in Example 5 which comprises 60% gamma-tocopherol and 28% delta-tocopherol.

In vivo evaluation of anti-inflammatory activity can be determined by well characterized assays such as reduction of carrageenan-induced paw edema in rats (Gabor, M., *Mouse Ear Inflammation Models and their Pharmacological Applications,* 2000). Carrageenan-induced paw edema is a model of inflammation, which causes time-dependent edema formation following carrageenan administration into the intraplantar surface of a rat paw. In studies carried out in support of the present invention, gamma-tocopherol, given orally to rats as a 10–100 mg/kg oral pretreatment over 3 days significantly reduced IL-6 levels in the edematous fluid in this model (Example 6).

U.S. Pat. No. 6,040,147 describes both prognostic and diagnostic applications of the measurement of levels of particular molecules including certain cytokines (e.g. interleukins 1–17) and cellular adhesion molecules (e.g. sICAM, integrins, ICAM-1, ICAM-3, BL-CAM, LFA-2, VCAM-1, NCAM and PECAM). The presence of such markers may be determined by methods well known in the art, including ELISA (enzyme linked immunosorbent assay) and other immunoassays and can be measured in body fluid, for example, blood, lymph, saliva and urine. U.S. Pat. No. 6,180,643 also describes the use of molecules such as IL-1, TNF-α as markers of IDDM and NDDM in particular, where certain therapies involve inhibiting the production of these molecules A correlation between SIRS/sepsis and certain tissue or serum markers have also been disclosed, including C-reactive protein (CRP) and neopterin. Serum procalcitonin (ProCT, also termed PAN-116) has recently been described as a clinical marker for systemic inflammation (U.S. Pat. No. 5,993,811) and U.S. Pat. App. No. 20010007022 describes in detail the use and preparation of antibodies to ProCT (or pCT) in both the therapy and detection of SIRS. Other cytokines which have been suggested as markers for SIRS include interleukin-10 (IL-10) and interleukin-6 (IL-6) (U.S. Pat. Nos. 6,103,702 and 6,203,997).

U.S. Pat. No. 5,496,832 describes in detail a rat model of immune mediated myocarditis in humans. The model is reproduced in brief below and can be used for testing a non-alpha-tocopherol composition of the present invention.

Briefly, male Lewis rats 300–350 g, are weighed and sedated with an i.p. injection of 20 mg of pentobarbital prior to baseline ECG recording. The rats are divided into four groups. The rats in Group 1 serve as a control group for rats developing myocarditis, and receive cardiac myosin only. The rats in Group 2 served as a control group for test compound and received test compound. The rats in Groups 3 and 4 are immunized with cardiac myosin and then treated with test compound.

The rats in Groups 1, 3 and 4, receive a subcutaneous injection in the left rear foot pad of 100 μg of porcine cardiac myosin, suspended in 0.1M phosphate buffered saline.

Seven days later, the rats in Groups 1, 3, and 4 are re-immunized with the same myosin concentration in the contralateral foot pad. Intraperitoneal administration of test compound is initiated on the first day of immunization at 1 mg/kg/day (Group 3; n=10), and 12 mg/kg/day (Group 4; n=6), using vehicle (20% dimethyl acetamide, 10% Tween 80, and 70% polyethylene glycol) and is maintained daily for fourteen days. The rats in Group 1 (n=10), received an i.p. injection of vehicle alone daily for fourteen days. The rats in Group 2 (n=7) are not immunized, but received a fourteen day daily i.p. regimen of test compound.

ECGs are obtained according to the following procedure. All animals are shaved in the area of the ventral cervical thorax, the right dorsal pelvic girdle and the ventral pelvic girdle. They are identically marked at the four standard ECG limb electrode sites (right and left fore limbs, right and left hind limbs), and the standard dorsal posterior ground electrode site with a tattoo marker; and, using a recorder with a chart speed of 100 mm/sec, a baseline day 0 lead II ECG is obtained. The tattoo marks served as permanent reference points for future recording.

Electrocardiographic profiles are obtained on days 7, 14, 21 and 28. In each instance, they are compared to the individual's baseline ECG and to the corresponding day ECG of Group 2. Initial and terminal heart rates are determined, and the mean values in millimeters, of the following standard ECG variables are obtained by caliper measurement of four different cardiac complexes per individual record.

1)—QRS complex length (msec)
2)—$Q_\alpha$ T segment length (msec)
3)—R—R segment length (msec)
4)—Heart Rate (beats/min)

On day 28, all surviving animals are anesthetized with an i.p. injection of 20 mg pentobarbital, weighed, and final ECGs are obtained. They are then euthanized by excess $CO_2$ inhalation, and the heart, spleen, right kidney and liver are inspected, removed, weighed and placed in sterile containers, containing 25 ml of 10% buffered formalin. Terminal heart weights are recorded as both individual values and as a ratio of heart to terminal body weight for all groups. Macroscopic evaluation of organs is achieved through application of the following gross pathology scoring system: 0)—no obvious hypertrophy or lesions; 1)—the presence of hypertrophy and/or a single well defined lesion; and 2)—the presence of hypertrophy and multiple lesions.

The hearts are removed from the formalin and a transversal cut is made immediately below the atrioventricular groove; the ventricles are then embedded in paraffin, for sectioning and staining. A microtome is used to cut 5 μm thick sections which are immediately stained with hematoxylin and eosin, and examined with a microscope at 100× and 400× magnification. Approximately seven sections per ventricle are evaluated to ensure uniformity and to determine a mean histopathologic score for individual animals of both control and experimental groups. There are no discernible differences among these sections for any individual animal examined. Photomicrographs are obtained. Microscopic evaluation of cardiac tissue is achieved through application of the following system:

0)—no lymphocytic infiltration visible throughout myocardium.
1)—moderate infiltration within an area not exceeding 0.25 $mm^2$.
2)—moderate or multiple infiltration within an area <4.0 $mm^2$.
3)—multiple infiltrates within an area>4.0 $mm^2$.

U.S. Pat. No. 5,780,237 describes a diagnostic assay for SRS, ARDS, sepsis, and MODS based on determining the levels of selected unsaturated and saturated free fatty acids (FFA) in a body fluid and determining a ratio value comprising the sum of the unsaturated FFAs divided by the sum of the saturated FFAs. The unsaturated FFAs include linoleate, oleate, arachinonate and the saturated FFAs include myristate, palmitate, stearate.

Animal Model of SIRS/Sepsis

In vivo animal models of SIRS/sepsis are known in the art and may be used to determine the efficacy of non-alpha-tocopherol enriched tocopherol compositions or treatment protocols. As described in detail in U.S. Pat. No. 6,103,702 and briefly described here, one such model in the rat uses a model of chronic peritoneal sepsis that results in systemic inflammatory response syndrome (SIRS). Sepsis is induced under pentobarbital anesthesia (50 mg/kg) in each rat by intraperitoneal (ip) injection of 200 mg/kg rat cecal contents mixed as a slurry in 5% dextrose in water (D5W). The cecal slurry is prepared from fresh cecal contents of a donor rat and is used within two hours of collection to induce sepsis. Non-septic controls receive an equivalent volume ip injection of D5W. Polyethylene catheters (Intramedic PE-50, Baxter, Deerfield, Ill.) are inserted into the right internal jugular vein and right carotid artery. The jugular catheter is used for venous access (drug infusions; volume replacement, etc). The carotid catheter is used to obtain arterial blood samples, and to monitor arterial blood pressure and heart rate. The catheters are secured in their respective vessels, tunneled subcutaneously to exit in the interscapular region, and filled with heparinized saline (50 units/ml 0.9% normal saline). Incisions are closed in layers using 3-0 silk. Rats are allowed to recover from anesthetic and provided food and water ad libitum.

The model of SIRS/Sepsis described above is associated with elevated concentrations of tumor necrosis factor alpha (TNF-α). The efficacy of treatment in vivo may be determined through monitoring the level of TNF-α in tissues such as spleen and liver or in serum as described in detail in U.S. Pat. No. 6,103,702, and briefly described below.

Serum and tissue tumor necrosis factor-alpha (TNF-α) concentrations are determined by enzyme-linked immunosorbant assay (ELISA). Samples of serum, liver, and spleen are collected, rapidly weighed, and frozen in liquid nitrogen. On the day of assay, tissues are added to labeled tubes containing lysis buffer (volume=10 ml/g wt. with 1:10 dilution) and kept on ice. The lysis buffer is 20 mM Tris (pH 7.4) containing 170 l/ml phenylmethylsulfonylflouride (PMSF), 0.5 g/ml leupeptin, 0.7 g/ml pepstatin, and 2.0 g/ml aprotinin to inhibit proteases. Samples are immediately homogenized using five 3 sec bursts, washing grinding pistol (3×) between samples with phosphate buffered saline. Samples are then centrifuged for 20 min at 2200 RPM, 4° C. The supernatant is removed and used for TNF-α measurements. Briefly, each microplate well contained 50 μl of assay diluent. To each well, 50 μl of standard, control, or serum/homogenate supernatant sample are added and mixed on an orbital plate shaker. Plates are incubated at room temperature for 2 hours. Each well is then aspirated and washed with wash buffer 4 times. After final aspiration of wash buffer, 100 μl of rat TNF-α conjugate is added to each well. Wells are then covered and incubated for 2 hours at room temperature. At the end of the incubation, the aspiration/wash procedure is repeated 4 times, after which 100 μl of stabilized chromogen solution is added to each well. Next, plates are incubated for 45 minutes at room temperature in a dark area. After this final incubation period, 100 μl stopping solution is added to each well. Optical density of each well at 450 nM is determined within 30 minutes using a Biotek Instruments (Winooski, Vt.) EL312e microtiter plate reader. Concentrations of TNF-α are calculated from the standard curves.

A TH2-specific gene which encodes a protein (STIF) differentially expressed within the TH2 cell sub-population has been reported as linked to proliferative and T-lymphocyte-related disorders such as chronic inflammatory diseases and disorders as well as atopic conditions such as asthma (U.S. Pat. No. 6,190,909). U.S. Pat. No. 6,190,909 describes in detail a variety of uses for STIF and STIF-related molecules.

A number of cytokines, such as tumor necrosis factor alpha (TNF-α), interleukin-1β, -6 and/or -8 (IL-1β, IL-6, IL-8) have been implicated in the mediation of inflammation associated with ARDS and asthma (U.S. Pat. No. 6,180,643). Both TNF-α and IL-1 are pro-inflammatory cytokines whose elevated levels over basal have been implicated in mediating or exacerbating both asthma and ARDS as well as other inflammation-associated conditions. Thus, as is known in the art and described in greater detail in U.S. Pat. No. 6,180,643, these molecules may be used as markers for the presence of such conditions as well as in the screening for non-alpha-tocopherol enriched tocopherol compositions which ameliorate conditions such as asthma and ARDS. In particular, assays designed to measure the inhibition of the production of TNF-α and IL-1β, by test compounds can be used to screen for effective treatments.

Models and protocols for determining the efficacy of treatments for conditions associated with pulmonary or respiratory inflammation are known in the art (e.g. U.S. Pat. Nos. 6,193,957; 6,051,566; 5,080,899, 6,180,643, 6,028,208 and U.S. Pat. App. Nos. 20010000341, 20010006656). In addition, U.S. Pat. App. No. 20010004677 describes a method and apparatus for measuring pulmonary stress. U.S. Pat. No. 6,193,957 describes in detail an in vivo model in sheep of pulmonary airflow resistance. The sheep are characterized as dual responders. The model is described in brief below.

Allergic sheep with previously documented dual bronchoconstrictor response to *Ascaris suum* antigen are used. The sheep are intubated with a cuffed nasotracheal tube and pulmonary airflow resistance ($R_I$) is measured by the esophageal balloon catheter technique, while thoracic gas volume is measured by body plethysmography. Data are expressed as specific $R_L$ ($SR_L$, defined as $R_L$ times thoracic gas volume ($V_{tg}$)).

To assess airway responsiveness, cumulative dose-response curves to inhaled cabachol are performed by measuring $SR_L$ before and after inhalation of buffered saline and after each administration of 10 breaths of increasing concentrations of carbachol (0.25, 0.5, 1.0, 2.0 and 4.0% wt/vol solution). Airway responsiveness is measured by determining the cumulative provocation dose ($PD_{400}$) of carbachol (in breath units) that increased $SR_L$ to 400% above baseline. One breath unit is defined as one breath of 1% carbachol solution. Each animal's baseline airway responsiveness ($PD_{400}$) is determined, and then on different experimental days the sheep undergo airway challenge with *Ascaris suum* antigen. $SR_L$ is measured, before and immediately after challenge, and then hourly for 8 hours. The post-challenge $PD_{400}$ is measured 24 hours after antigen challenge when AHR occurred. The protocol is repeated at least 14 days later, but each animal is administered a dose of one of the test drug fractions either about 30 minutes before antigen challenge or immediately after post-challenge $SR_L$ measurement.

U.S. Pat. No. 6,051,566 describes in detail protocols for studies of non-specific bronchial hyperreactivity in patients. U.S. Pat. No. 5,080,899 details a in vivo guinea pig model for studying the efficacy of orally administered drugs for the treatment of pulmonary inflammation. The model is described in brief below.

Male Hartley guinea pigs (400–700 g) that have been fasted overnight are sensitized according to a modification of the method of Dunn et al (1988 *Am. Rev. Resp. Dis.* 137: 541). Guinea pigs receive 1 i.m. injection in each hind leg of 0.35 ml (total volume=0.7 ml) ovalbumin (OA; 50 mg/ml), in isotonic sterile saline. Following a 3 week sensitization period, each animal is pretreated (−1 h) with pyrilamine (2.5 mg/kg i.p.) to prevent hypoxic collapse and death, and then challenged with an aerosol of 0.2% OA (in distilled deionized water) for 3 min using a DeVilbiss Ultra-Neb 100 nebulizer. Drugs or vehicle (0.5% Tween 80) are administered orally in a volume of 1 ml/500 g body wt. at appropriate times pre- and post-OA challenge. A test compound is administered orally at −48 h, −24 h, −1 h and +4 hours relative to OA aerosol. Positive control animals are challenged with the OA aerosol, and negative control animals are challenged with an aerosol of distilled water only.

Twenty-four hours later, each animal is humanely sacrificed with an overdose of urethane (60 mg/ml, ≈10 ml i.p.). The trachea of each animal is isolated and the lungs are lavaged in situ with three-20 ml washes if isotonic sterile saline. All samples are kept on ice. This bronchoalveolar lavage fluid from each animal is then centrifuged for 10 min at 400×g at 5° C. The supernatant is discarded, and each cell pellet is resuspended in 3 ml of isotonic sterile saline. The number of inflammatory cells present is then determined using a Coulter model ZM particle counter (Beckman Coulter, Inc., Fullerton, Calif.).

All values are corrected by subtracting the mean (x) value of the negative control group from all other individual samples. Percent inhibition values for individual samples are calculated using these corrected cell counts in the following formula:

$$\% \text{ Inhibition} = \frac{\bar{x} \text{ positive control (corrected)} - \text{individual cell count (corrected)}}{\bar{x} \text{ positive control (corrected)}} \times 100$$

Mean % inhibition is determined for each group and expressed as x% inhibition±S.E. The $ED_{50}$s with 95% confidence limits are calculated (Litchfield et al., 1949 *J. Pharmacol. Exp. Ther.* 96: 99–113).

U.S. Pat. App. Nos. 20010000341 and 20010006656 describe in vivo models of LPS-induced airway inflammation in mice. U.S. Pat. No. 6,028,208 describes a similar in vivo model of LPS-induced airway inflammation in hamsters.

The effect of test compounds in the treatment of chronic obstructive pulmonary disease can be tested in a murine model of pulmonary neutrophilia induced by lipopolysaccharide via intranasal instillation. Bacterial lipopolysaccharide (LPS) is a macromolecular cell surface antigen of bacteria which, when applied in vivo triggers a network of inflammatory responses. The main characteristics of this LPS-induced lung inflammation model, macrophage activation, tumor necrosis factor-alpha (TNF-α) production and neutrophil infiltration and activation, are features of chronic obstructive pulmonary disease. This model causes pulmonary inflammation as an acute injury which occurs after 2 to 4 hours in the airway lumen, where all the inflammatory parameters can be assessed by bronchoalveolar lavage (BAL).

As described in U.S. Pat. App. No. 20010000341, a test compound is dissolved in dimethyl sulfoxide (DMSO) and to the resulting solution is added sterile phosphate buffered saline (PBS) (50 µl). The final concentration of DMSO is 2%. Female Balb/C mice (20–25 g) are treated intranasally, under halothane/oxygen/nitrous oxide anaesthesia, with the PBS DMSO diluent containing the test compound at a suitable dose (0.1–30 mg/kg) or with diluent alone and, 30 minutes later, with 0.3 mg/kg of LPS (Salmonella Typhosa, Sigma). The animals are housed in plastic cages in an air conditioned room at 24° C. Food and water are available ad libitum. Three hours after intranasal administration of LPS, terminal anesthesia is induced with pentobarbitone sodium (60 mg/kg, i.p.), the abdominal cavity is opened and the animals are exsanguinated by withdrawal of blood from a major blood vessel.

The trachea is cannulated and bronchoalveolar lavage (BAL) is performed by injecting 4×0.3 ml of PBS into the lung via the trachea. The fluid is then immediately withdrawn and the cell suspension stored on ice. Total cell count is measured and cytospin preparation (Shandon Scientific Ltd, Cheshire, UK) prepared. Cells are stained with Dif-Quick (Baxter Dade AG, Dudingen, Switzerland) and a differential count of 200 cells performed using standard morphological criteria. The remaining lavage fluids are centrifuged at 1200 rpm for 10 minutes, the supernatant is aliquoted and stored at −80° C.

BAL myeloperoxidase (MPO) activity is measured on fresh BAL supernatant using a 96 well plate format colorometric assay. 50 µl of the samples, in duplicate, are mixed with 100 µl of the substrate buffer for 5 minutes at room temperature (sodium phosphate 50 mM, pH 6.0 containing 0.5% hexadecyltrimethylammonium bromide, 0.167 nM o-dianisidine dihydrochloride and 0.4 mM $H_2O_2$). The reaction is stopped with 100 µl of 5% sodium azide in distilled water and the optical density (OD) read at 450 nm. Results are expressed as U/ml using a standard curve established with human leukocyte myeloperoxidase (Sigmna, St. Louis, Mo.).

The inhibitory effect of the compound under test on lung inflammation is shown by the reduced neutrophil count and/or reduced MPO activity obtained after administration of the compound compared with that obtained after administration of diluent alone. As described in U.S. Pat. No. 6,028,208, a male golden hamster is placed in an inhalation chamber (volume: 12 liter) and allowed to inhale LPS (nebulizer filled concentration: 2.0 mg/ml) generated by an ultrasonic nebulizer for 30 min to cause airway inflammatory. Just after the inhalation of the LPS, a test compound is administered through intrarespiratory tract administration or orally under halothane anesthesia. After 24 hr, tracheal branches and pulmonary alveoli are washed, and the number of neutrophils in the washing are determined. Using the number of neutrophils obtained in the absence of a test compound as the control, the decreasing rates of the numbers of neutrophils are expressed in terms of percent suppression based on the control.

This model is widely used as an inflammatory pulmonary disease model (Esbenshade et al., 1982 *J. Appl. Physiol.* 53:967–976), and it has been reported that the model exhibits a morbid state of acute aggravation of an inflammatory pulmonary disease (Hurlar et al., 1983 *J. Appl. Physiol.* 54:1463–1468).

U.S. Pat. No. 6,180,643 describes in detail several assays which are used to characterize the ability of compounds to inhibit the production of TNF-α and IL-1β.

Test compounds can also be tested for anti-inflammatory properties in models of inflammation including the carageenan paw edema model (Winter et al 1962 *Proc. Soc. Exp. Biol. Med.* 111:544; Swingle, in R. A. Scherrer and M. W. Whitehouse, Eds., 1974 Antiinflammatory Agents, *Chemistry and Pharmacology*, Vol. 13-II:33, Academic, New York) and collagen induced arthritis (Trentham et al 1977 *J. Exp. Med.* 146:857; Courtenay 1980 *Nature (New Biol.)* 283: 666).

Anti-islet cell antibodies (ICAS) have been suggested as markers of IDDM, being present up to 10 years prior to the clinical manifestation of the disease (Nathan, supra). U.S. Pat. No. 6,057,097 also describes in detail methods for using anti-nuclear auto-antibodies (ANAs) associated with IDDM for prognostic and diagnostic applications.

A TH2-specific gene which encodes a protein (STIF) differentially expressed within the TH2 cell sub-population has been reported as linked to proliferative and T-lymphocyte-related disorders such as chronic inflammatory diseases and disorders including IDDM (U.S. Pat. No. 6,190,909).

It has been reported (Spanheimer supra) that diabetes may lead to a chronic, low-grade inflammatory state possibly caused by glycosylation of proteins that activate macrophages or by increased oxidative stress. A marker for systemic inflammation is C-reactive protein (CRP; U.S. Pat. No. 6,040,147) and some studies have found that the levels of CRP are elevated in IDDM patients without macrovascular disease. These findings have led researchers to suggest that CRP may serve as a marker for tracking inflammation (Spanheimer supra; Ridker et al. 2001 *N. E. J. M.* 344(26): 1959–1965).

U.S. Pat. No. 5,789,652 is directed to a non-insulin dependent diabetic rat which can be used to determine the efficacy of test compounds in the treatment of NIDDM. U.S. Pat. No. 5,877,203 describes in detail the use of cholesterol fed rabbits for modeling the efficacy of a test compound on the binding of monocytes to the thoracic aorta. U.S. Pat. No. 6,261,606 describes several animal models of diabetes, (IDDM, NIDDM and steroid-induced) for use in screening the efficacy of test compounds in the treatment of these conditions. Description of these models is reproduced below in brief.

Streptozotocin Rats—Model for IDDM. (U.S. Pat. No. 6,261,606)

Sprague Dawly male rats weighing 120–130 g are injected subcutaneously with a single dose of streptozotocin (60 mg/kg body weight) in 0.5 ml citrate buffer, 0.05 M pH 4.5. Plasma glucose concentrations are measured seven days later using a commercial glucometer. Animals with blood glucose higher than 250 mg/dl are chosen for the subsequent tests with test compounds. Test compounds are introduced orally. Blood is collected from the tail vein at intervals of 30 min, and levels of glucose, free fatty acids and triglycerides are measured as known in the art. Mirsky 1993 *J. Inorg. Biochem.* 49:123–128.

Sand Rats and Spiny Mice—Models for NIDDM. (U.S. Pat. No. 6,261,606)

Sand rats (*Psammomys obesus*) and Spiny mice (*Acomys rusatus*), when fed a high energy diet, develop NIDDM. Schmidt-Nielsen et al., 1964 *Science* 143: 689–690. Such models can be used to test non-alpha-tocopherol compositions of the present invention for their ability to reduce symptoms of inflammation associated with NIDDM, including a reduction in the levels of one or more inflammatory markers, such as for example, CRP.

Steroid-induced Diabetes in Rats. (U.S. Pat. No. 6,261,606)

Corticosteroid treatment often leads to impaired glucose tolerance and diabetes. Merck manual, 14th ed. Rahway, N.J.: Merck Sharp and Dohme Research Laboratories, 1982, 2385. Steroid diabetes is characterized by insulin resistance in the absence of ketosis and acidosis.

Formulations of the invention are tested for efficacy in various cellular models of inflammation that are known in the art. For example, E-selectin (also called Endothelial Leukocyte Adhesion Molecule, or ELAM) is a cell adhesion molecule that is actively expressed on the surface of endothelial cells, where it helps mediate the initial attachment of circulating leukocytes. It therefore serves as a sensitive and specific marker of inflammation. Cell assays have been devised to measure the ability of test compounds to reduce expression of E-selectin by endothelial cells that are subjected to inflammatory situli, such as lipopolysaccharides and interleukin-1β (IL-1B). Test compounds that inhibit this response have anti-inflammatory properties. Such an assay is described in Example 1B herein; other assays protocols are known in the art. (See, e.g. Hess, D. C., et al. Neursci. Lett. 213(1): 37–40, 1996). Compositions of the present invention can be tested in such an assay for their ability to reduce expression of E-selectin.

Non-alpha-tocopherol enriched tocopherol compositions of the present invention are further tested in a model of muscle performance, as described in Example 3 herein. Briefly, human subjects who are not customarily involved in weight training are given either placebo or a pre-determined daily dose of a non-alpha-tocopherol enriched formulation of the invention. Blood metabolites and inflammatory markers are measured prior to and at defined time intervals after eccentric exercise (for example, a defined arm "curl") on an exercise machine. Subjective pain assessment is also taken. Anti-inflammatory tocopherol formulations provide reduction in at least one or more markers of inflammation, as defined herein, or reduction in pain, as compared to placebo-treated control subjects.

Methods of Using Compounds of the Invention

The compositions of the present invention are administered to a mammalian subject to reduce elevated levels of an inflammatory marker, including for example CRP, associated with inflammation or to maintain and promote healthy and/or normal levels of inflammatory markers associated with inflammation, such as, for example, CRP, certain cytokines associated with inflammation as described herein, such as for example, IL-6, TNF-α and B61 that are associated with inflammation in said subject. Healthy or normal ranges of such inflammatory markers are known in the art. See for example, U.S. Pat. No. 6,040,147 which provides healthy or normal ranges for CRP. For example, non-alpha-tocopherol enriched compositions and/or non-alpha-tocopherol metabolite enriched compositions of the present invention are administered to a mammalian subject at risk for developing inflammation associated with diseases or disorders disclosed herein, such as, for example, ESRD, in order to maintain healthy or normal levels of CRP. The compositions of the present invention are administered to a mammalian subject to reduce elevated levels of proteins associated with inflammation, such as, for example, CRP, certain cytokines associated with inflammation as described herein, TNF-α and B61 that are associated with inflammation in said subject.

In some examples of the present invention, a gamma-tocopherol enriched tocopherol composition and/or a gamma-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; and periodontal disease.

In some examples of the present invention, a beta-tocopherol enriched tocopherol composition and/or a beta-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; periodontal disease and inflammatory skin conditions.

In other examples of the present invention, a delta-tocopherol enriched tocopherol composition and/or a delta-tocopherol metabolite enriched composition are used in methods for the treatment and/or amelioration of a symptom of inflammation, such as in methods for reducing CRP levels associated with the inflammation, including respiratory inflammatory conditions, such as SIRS, ARDS, AHR, and asthma; sepsis; diabetes; muscle fatigue; systemic lupus erythematosis (SLE); renal inflammation, including in ESRD; periodontal disease and non-psoriatic inflammatory skin conditions.

In further examples, methods of the present invention relate to treating or ameliorating the symptoms of end stage renal disease (ESRD) in a mammalian subject at risk for or subject to inflammation associated with ESRD by administering an amount of a gamma-tocopherol enriched tocopherol composition or a gamma-tocopherol metabolite enriched composition effective to reduce the levels of an inflammatory marker, such as for example CRP and/or effective to ameliorate the symptoms of the condition(s) or minimize the extent and/or severity of the inflammation associated with or due to the condition by ameliorating or reducing the inflammation that would otherwise occur. The methods encompass administering a gamma-tocopherol enriched tocopherol composition and/or a gamma-tocopherol metabolite enriched composition to an individual subject to ESRD. The amount administered and the duration of the treatment are effective to minimize the size and/or severity of the inflammation associated with the condition in the mammalian subject as measured by for example, the level of particular cellular adhesion molecules associated with inflammation; cytokines associated with the inflammation, such as IL-6 or CRP associated with the condition. Thus, it is anticipated that as a result of such treatment the size and/or severity of any symptoms associated with the inflammation that develops is minimized. Patients having end-stage renal disease (ESRD) have no or very minimal renal function and are therefore incapable of natriuresis. Kidney function is provided by artificial kidney dialysis. Inflammatory markers, including serum CRP levels are markedly elevated in dialysis patients, as is the cardiovascular mortality rate. Moreover, CRP is a significant predictor of cardiovascular and all-cause mortality in dialysis patients (Foley R N, et al., *J Am Soc Nephrol* 1998;9:S16–23; Handelman G J, et al., *Kidney Int* 2001;59:1960–6; Zimmerman J, et al., *Kidney Int* 1999;55:648–58; Iseki K, et al., *Nephrol Dial Transplant* 1999;14:1956–60).

In studies carried out in support of the present invention, as detailed in Example 5, administration of a gamma-tocopherol enriched tocopherol composition further comprising delta-tocopherol resulted in a decrease in inflammatory markers, exemplified by serum CRP and IL-6, within 2 weeks of initial treatment.

The compositions, as described above, can be prepared as a medicinal preparation (such as an aqueous solution for injection) or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube to burn victims (referred to as enteral administration or gavage administration). A "dietary supplement" shall mean a product that is intended to supplement the human diet and is typically provided in the form of a pill, capsule, tablet or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote tissue health or to prevent inflammation. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration of the particular formulation can vary based on the individual subject, the stage of disease, and other factors evident to one skilled in the art. During the course of the treatment, the concentration of the subject compositions may be monitored to insure that the desired level is maintained.

Generally, the route(s) of administration useful in a particular application are apparent to one of skill in the art. Routes of administration include, but are not limited to, oral, topical, dermal, transdermal, transmucosal, epidermal, parenteral, gastrointestinal.

For in vitro or ex vivo administration, the compounds may be provided in the medium of the cells and/or organ, as a single bolus, by repetitive addition, by continual infusion, or the like.

For administration, the invention includes subject compositions suitable for oral administration including, but not limited to, pharmaceutically acceptable tablets, capsules, powders, solutions, dispersions, or liquids or compounded with other physiologically acceptable materials which can be ingested including, but not limited to, foods, including, but not limited to, food bars, beverages, powders, cereals, cooked foods, food additives and candies. For rectal administration, the subject compositions may be provided as suppositories, as solutions for enemas, or other convenient application. Otherwise, the subject compositions may be administered intravascularly, arterially or venous, subcutaneously, intraperitoneally, intraorganally, intramuscularly, by dermal patch, or the like.

For administration, the formulations may conveniently be presented in unit dosage form and may be prepared by any methods well known in the art of pharmacy. Such methods include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

When the composition is incorporated into various media such as foods, it may simply be orally ingested. The food can be a dietary supplement (such as a snack or wellness dietary supplement) or, especially for animals, comprise the nutritional bulk (e.g., when incorporated into the primary animal feed).

The amount of the composition ingested, consumed or otherwise administered will depend on the desired final concentration. Typically, the amount of a single administration of the composition of the invention can be about 0.1 to about 1000 mg per kg body weight, or about 0.5 to about 10,000 mg per day. Any of these doses can be further subdivided into separate administrations, and multiple dosages can be given to any individual patient. A typical dosage for vitamin E administration is 100–600 mg/day for an adult human. However, various different dosages are described in scientific publications; see, for example, Ng et al. (1999) *Food Chem. Toxicol.* 37: 503–8; Ko et al. (1999) *Arch. Phys. Med. Rehabil.* 80: 964–7; Chen et al. (1999) *Prostaglandins Other Lipid Mediat.* 57: 99–111; and Thabrew et al. (1999) *Ann. Clin. Biochem.* 36: 216–20.

To determine the optimum concentration for any application, conventional techniques may be employed. Thus, for in vitro and ex vivo use, a variety of concentrations may be used and various assays employed to determine the degree of inflammation.

The subject compositions may be administered parenterally including intravascularly, arterially or venous, subcutaneously, intradermally, intraperitoneally, intraorganally, intramuscularly, or the like.

Formulations for parenteral administration include aqueous and non-aqueous isotonic sterile injection solutions which may contain buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

For topical administration, the subject compositions may be provided as a wide variety of product types including, but are not limited to, lotions, creams, gels, sticks, sprays, ointments and pastes. These product types may comprise several types of formulations including, but not limited to solutions, emulsions, gels, solids, and liposomes.

Compositions useful for topical administration of the compositions of the present invention formulated as solutions typically include a pharmaceutically-acceptable aqueous or organic solvent. The terms "pharmaceutically-acceptable organic solvent" refer to a solvent which is capable of having a non-alpha-tocopherol composition and/or metabolite and/or derivative thereof, or mixtures of tocopherols, thereof, dispersed or dissolved therein, and of possessing acceptable safety properties (e.g., irritation and sensitization characteristics). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, ethanol, isopropanol, butanediol, and mixtures thereof.

If the topical compositions useful in the subject invention are formulated as an aerosol and applied to the skin as a spray-on, a propellant is added to a solution composition. Examples of propellants useful herein include, but are not limited to, the chlorinated, fluorinated an chloro-fluorinated lower molecular weight hydrocarbons.

Topical compositions useful in the subject invention may be formulated as a solution comprising an emollient. As used herein, "emollients" refer to materials used for the prevention or relief of dryness, as well as for the protection of the skin. A wide variety of suitable emollients are known and may be used herein.

Another type of product that may be formulated from a non-alpha-tocopherol enriched tocopherol composition and/or a non-alpha-tocopherol metabolite enriched composition is a cream. Another type of product that may be formulated from a subject solution is a lotion.

Yet another type of product that may be formulated from a composition of the present invention is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble.

Another type of formulation is an emulsion. Emulsifiers may be nonionic, anionic or cationic and examples of emulsifiers are described in, for example, U.S. Pat. Nos. 3,755,560, and 4,421,769.

Lotions and creams can be formulated as emulsions as well as solutions.

Single emulsions for topical preparations, such as lotions and creams, of the oil-in-water type and water-in-oil type are well-known in the art. Multiphase emulsion compositions, such as the water-in-oil-in-water type, are also known, as disclosed, for example, in U.S. Pat. No. 4,254,105. Triple emulsions are also useful for topical administration of the present invention and comprise an oil-in-water-in-silicone fluid emulsion as disclosed, for example in U.S. Pat. No. 4,960,764.

Another emulsion useful in the topical compositions is a micro-emulsion system. For example, such a system comprises from about 9% to about 15% squalane, from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water.

Liposomal formulations are also useful for the compositions of the present invention. Such compositions can be prepared by combining non-alpha-tocopherol, and/or metabolite thereof, and/or derivative thereof, and/or mixtures thereof, with a phospholipid, such as dipalmitoylphosphatidyl choline, cholesterol and water according to known methods, for example, as described in Mezei et al. (1982) *J. Pharm. Pharmacol.* 34:473–474, or a modification thereof. Epidermal lipids of suitable composition for forming liposomes may be substituted for the phospholipid. The liposome preparation is then incorporated into one of the above topical formulations (for example, a gel or an oil-in-water emulsion) in order to produce the liposomal formulation. Other compositions and pharmaceutical uses of topically applied liposomes are described for, example, in Mezei (1985) *Topics in Pharmaceutical Sciences*, Breimer et al. eds., Elsevier Science, New York, N.Y., pp. 345–358.

For rectal administration, the subject compositions may be provided as solutions for enemas, as suppositories with a suitable base comprising, for example, cocoa butter or a salicylate, or as other convenient applications.

Formulation for vaginal administration may be presented as pessaries, tampons, creams, gels, pastes, foams or spray formulations containing in addition to the active ingredient such carriers as are known in the art to be appropriate.

To determine the optimum concentration for any application, conventional techniques may be employed. Thus, for in vitro and ex vivo use, a variety of concentrations may be used and various assays employed to determine the degree of dysfunction of the cells when exposed to stress. Examples of such assays are described herein and have been described, for example, in U.S. Pat. No. 5,801,159.

The above-mentioned compositions and methods of administration are meant to describe but not limit the methods and compositions of the present invention. The methods of producing various compositions and devices are within the ability of one skilled in the art and are not described in detail here.

The non-alpha-tocopherol enriched tocopherol compositions, and/or non-alpha-tocopherol metabolite enriched compositions of the present invention, and methods using the compositions are capable of reducing the level of inflammatory markers associated with inflammation, such as for example, CRP and IL-6. These conditions can be induced experimentally by chemical interference or by changing the environmental conditions in the laboratory (e.g., by inducing anoxia, hypothermia, hyperthermia, etc.).

Various assays, compositions and methods useful for identifying compositions and methods for reducing tissue damage are provided in the Examples.

The following examples are provided to illustrate, but not limit, the invention.

EXAMPLES

Example 1

Cellular Inflammation

This example provides exemplary assays for measuring inflammatory reaction in a cell line. Specifically, this assay provides a predictive measure of anti-inflammatory activity of formulations of the present invention.

A. Human Hep3B Cells—CRP assay. Hep3B Cell Line is obtained from the American Type Culture Collection (ATCC Catalog No. HB-8064). The Hep3B cell line was derived from liver tissue of an 8-year-old Black male. The cells are epithelial in morphology and produce tumors in nude mice. The cells produce $\alpha$-fetoprotein, hepatitis B surface antigen, albumin, $\alpha$-2-macroglobulin, $\alpha$-1-antitrypsin, transferrin, plasminogen, complement C3 and $\beta$-lipoprotein (Knowles B B, et al., Science, 1980, 209:497–499). This cell line has been widely used to study hepatocyte cytokine and acute phase protein release (e.g., Damtew B, et al., 1993, *J Immunol* 150:4001–4007).

HEP3B cells are grown in Minimum Essential Medium (MEM; GIBCO) supplemented with 10% Fetal Bovine Serum (FBS; Hyclone), 1× Penicillin/Streptomycin (GIBCO, Cat #. 15140-122) and 0.1 mM non-essential amino acids (GIBCO, Catalog No. 11140-050). Cells are thawed and transferred to warm medium according to standard methods known in the art.

Cells are incubated in flasks at 37° C. with 5% $CO_2$ in an air atmosphere incubator. HEP3B growth media is changed every 2 days until the cells reach 70–80% confluence (approx. 3–4 days). For assay, the cells are transferred to 96-well plates, seeded at 5000 cells per well in culture media, and left to grow for 7 days in a 37° C. incubator (air supplemented with 5% $CO_2$). Media is replaced daily until assay.

Test compounds are diluted into "Stimulus Buffer" (MEM medium containing 0.1 mM non-essential amino acids, 1× penicillin/streptomycin, 10% FBS with 10 ng/ml IL-1β, 20 ng/ml IL-6 and 1 μM dexamethasone. Media is removed from the cells and is replaced with 200 μl of test dilution. Cells are returned to the incubator for three days at 37° C. CRP ELISA is then performed on supernatant from the cells, as described below.

Costar EIA/RIA plates are coated with rabbit anti-human CRP (DAKO) diluted 1:4000 in carbonate buffer (100 μl/well) for 45 minutes at 37° C. Plates are then washed 5× with CRP washing buffer (50 mM Tris-HCl, 0.3M NaCl, 0.5 Ml Tween-20, pH 8.0) using an automatic plate washer. Plates may be dried, covered and refrigerated until use. Supernatant (100 μl) is removed from each well of the test plates and added to the corresponding well of a precoated ELISA plate.

100 μl HRP-conjugated rabbit anti-human CRP (DAKO) diluted 1:500 (in CRP wash buffer) is added to each well, followed by incubation for 30 minutes at 37° C. Plates are washed 5× with CRP washing buffer using the automatic plate washer. 200 μl of 3,3',5,5'-Tetramethyl Benzidine (TMB) liquid Substrate System (Sigma, St. Louis, Mo.) is added to each well, followed by incubation in the dark for 15 minutes at room temperature. Finally, 50 μl of 1M $H_2SO_4$ is added to each well and absorbance at 450 nm is immediately measured in a microtiter spectrophotometer.

CRP measured as above is normalized to cell count per well, using a cell viability assay, such as the Cell Tracker Green assay. To do this, the remainder of the medium is from the cell test plates, cells are washed with 200 μl of pre-warmed 1× Hanks Basic Salt Solution (HBSS; GIBCO), and 100 μL of 5 μM Cell Tracker Green (Molecular Probes, Eugene, Oreg.) is added to each well. Plates are then incubated at 37° C. for 30 minutes. Cells are then washed twice with prewarmed 1× HBSS. Plates are immediately read using a Fluoroskan® flourometer with a 485 excitation/ 538 emission filter pair.

In a CRP assay such as the one disclosed herein, gamma-tocopherol was effective at reducing CRP levels by about 40% to about 60% at about 10 micromolar. In a CRP assay such as the one disclosed herein, beta-tocopherol was effective at reducing CRP levels by about 50% at about 3 to about 10 micromolar. In a CRP assay such as the one disclosed herein, delta-tocopherol at an $EC_{50}$ of between about 9 to about 15 micromolar was effective at reducing CRP levels. Other non-alpha tocopherols can be tested in this assay to determine their reduction of CRP levels.

Cell-ELAM Assay. Endothelial-Leukocyte Adhesion Molecule (ELAM), also known as E-selectin, is expressed on the surface of endothelial cells. In this assay, lipopolysaccharide (LPS) and IL-1β are used to stimulate the expression of ELAM; test agents are tested for their abilities to reduce this expression, in accordance with studies showing that reduction of leukocyte adhesion to endothelial cell surface is associated with decreased cellular damage (e.g., Takada, M., Et al., Transplantation 64: 1520–25, 1997; Steinberg, J. B., et al., J. Heart Lung Trans. 13:306–313, 1994).

Endothelial cells may be selected from any of a number of sources and cultured according to methods known in the art; including, for example, coronary artery endothelial cells, human brain microvascular endothelial cells (HBMEC; Hess, D. C., et al., Neurosci. Lett. 213(1): 37–40, 1996), or lung endothelial cells. Cells are conveniently cultured in 96-well plates. Cells are stimulated by adding a solution to each well containing 10 μg/ml LPS and 100 pg/ml IL-1β for 6 hours in the presence of test agent (specific concentrations and time may be adjusted depending on the cell type). Treatment buffer is removed and replaced with pre-warmed Fixing Solution® (100 μl/well) for 25 minutes at room temperature. Cells are then washed 3×, then incubated with Blocking Buffer (PBS+2% FBS) for 25 minutes at room temperature. Blocking Buffer containing Monoclonal E-Selectin Antibody (1:750, Sigma Catalog #S-9555) is added to each well. Plates are sealed and stored at 4° overnight. Plates are washed 4× with 160 μL Blocking Buffer per well. Second Antibody-HRP diluted 1:5000 in Blocking Buffer is then added (100 μL/well), and plates are incubated at room temperature (protected from light) for two hours. Plates are then washed 4× with Blocking Buffer before addition of 100 μL of ABTS Substrate solution at room temperature (Zymed, Catalog #00–2024). Wells are allowed to develop for 35 minutes, before measurement at 402 nm in a Fluoroskan® Reader with shake program for 10 seconds. Positive results are recorded as a decrease in ELAM concentration in tested wells, as compared to control wells.

In an ELAM assay, such as the one described herein, gamma-tocopherol at $EC_{50}$ in a range of 100–1000 micromolar, and in particular at 400 micromolar, was able to reduce the expression of ELAM. In an ELAM assay, such as the one described herein, delta-tocopherol $EC_{50}$ at a range of 300–1000 micromolar, and in particular at $EC_{50}$ at 600 micromolar, was able to reduce the expression of ELAM. Alpha-tocopherol was not active at 1000 micromolar. Other non-alpha tocopherol enriched tocopherol compositions or non-alpha-tocopherol metabolite enriched compositions can be tested in this assay to determine their reduction of CRP levels.

Example 2

In vivo Model of Cellular Inflammation

This assay measures the ability of test compounds to prevent or reduce inflammation secondary to oxazolone or arachidonic acid.

A. Arachidonic acid. Albino male CD-1 mice, 7–9 weeks old were used in this test. A 20% (w/v) arachidonic acid solution in acetone is prepared. Twenty microliters of the arachidonic acid solution is applied to the dorsal left ear of the mouse. Immediately thereafter, test compounds (20 μL in 70% ethanol/30% propylene glycol) are applied to the left ear. The untreated right ears served as control. Mice are sacrificed by $CO_2$ inhalation, one hour after treatment. The left and right ears are removed and 7 mm punch biopsies taken from each. The punch biopsies are weighed, and the differences calculated. Gamma-tocopherol was able to reduce inflammation secondary to exposure to arachidonic acid as measured in this assay. Other non-alpha-tocopherol enriched tocopherol compositions can be tested for their ability to reduce inflammation in this model.

B. Oxazolone. CD-1 mice are induced by applying 3% oxazolone (Sigma) (30 mg/ml prepared in corn oil:acetone)

to the shaved abdomen. Five days later, the mice are challenged with 2% oxazolone (20 mg/ml) in acetone on the left ear (right ear was untreated control). One hour after challenge, test compounds are applied to the left ear in 70% ethanol/30% propylene glycol. Animals are sacrificed 24 hours later and 7 mm ear punches are removed. The ear punches are placed on a balance scale, and the difference between the untreated and treated ears is determined. Percent inhibition is calculated by comparing the means of each group to the vehicle group. (Hydrocortisone serves as a positive control in this test.). Non-alpha-tocopherol enriched tocopherol compositions can be tested for their ability to reduce inflammation in this model.

Example 3

Muscle Inflammation

Healthy, non-exercising young male adults (aged 18–25) provide a sample of blood for baseline metabolite testing (defined below) and are given test article or placebo for seven days. Subjects then perform three sets of ten repetitions using 80% of their eccentric 1-repetition maximum on a Cybex® arm curl machine (Cybex International Inc., Medway, Mass.). The subject is given two minutes rest between sets, and repetitions continue until fatigue. Three days following exercise, subjects provide blood for testing of CBC and levels of metabolites and markers (isoprostanes, lipid hydroperoxides, LDH, CK, myoglobin, CRP, IL-6, myeloperoxidase), as well as tocopherol (compliance monitoring). Subjects also provide a subjective evaluation of muscle soreness. These indices are measured and collected again four days later.

Baseline levels of metabolites and markers are taken as the mean of values measured at intake and just prior to exercise; differences from baseline are calculated 3 and 7 days post exercise. Test compounds are considered to have an anti-inflammatory effect, if they produce a decrease in any of the inflammatory markers, in particular, CRP, compared to baseline or if they produce a reduction in the average increase measured in control (placebo-treated) subjects. Non-alpha-tocopherol enriched tocopherol compositions or non-alpha-tocopherol metabolite enriched compositions are tested for their ability to reduce inflammatory markers, such as for example, CRP levels in this model.

Example 4

Analysis of Serum Samples for Tocopherol and Tocopherol Metabolites

Materials.

Reagents. (+)-γ-tocopherol and (±)-α-tocopherol were purchased from Sigma (catalog #T-1782 and T-3251, respectively). γ- and α-tocopherol stock solutions were prepared individually in acetonitrile (4 mg/ml) and stored in amber vials at −80° C. γ-CEHC was prepared at Galileo Laboratories, Inc., according to methods known in the art, while α-CEHC was purchased from Encore Pharmaceuticals (Riverside, Calif., catalog #E-8201). γ- and α-CEHC stock solutions were prepared individually in acetonitrile (1 mg/ml) and stored in amber vials at −80° C. Acetonitrile and methanol used for extraction and HPLC were purchased from Burdick and Jackson. Acetic acid, ethanol, and hexane were obtained from EM Science. Butylated hydroxy toluene (BHT, catalog #B-1378), L-ascorbic acid (catalog #A-7631), *E. coli* β-glucuronidase (catalog #G-7396), trifluoroacetic acid, and monobasic potassium phosphate were purchased from Sigma. Pooled, frozen human serum and plasma with EDTA used for background subtraction and standards was obtained from Valley Biomedical (catalog #HS-1004 and HP-1051, respectively). Centricon YM-30 and YM-50 membrane filtration devices were obtained from Millipore Corp.

Instruments. Tocopherol analyses were conducted by LC-UV detection on an Agilent 1100 Series HPLC with diode-array detector using an Alltima $C_{18}$ HPLC column (5 μm, 150×2.1 mm) purchased from Alltech Associates, Inc. (catalog #88370). CEHC analyses were conducted by LC-MS on an Agilent 1100 Series LC-MSD with diode array detector and electrospray ionization (ESI) source using the same type of HPLC column. Solvent removal was achieved using a Speedvac SC210A centrifugal evaporator (Savant Instruments).

Methods.

Tocopherol Standards. Standard mixtures of γ- and α-tocopherol (1:1) in acetonitrile (10, 20, 50, 100, 500, 1000, and 2000 μg/mL each) were prepared from stock solutions on each day of analyses. Each standard mixture (10 μL) was added to 90 μL of pooled human serum to produce samples used to generate the standard curves (1, 2, 5, 10, 50, 100, and 200 μg/mL tocopherols).

Tocopherol Extraction. Ethanol (150 μL) was added to each standard serum sample prepared as described above and to each study subject serum sample (100 μL) to precipitate proteins, and then 250 μL water was added to increase the volume for extraction. Tocopherols were extracted with 2 mL of hexane/ethyl acetate (5:1). After vortexing, centrifugation, and freezing the sample at −80° C., the upper, organic layer was removed and the solvents evaporated. The residue was resuspended in 100 μL of acetonitrile/methanol (1:1) and used for HPLC analysis.

Tocopherol Analysis. Extracted tocopherols were separated by HPLC (25 μL injection) using an Alltima $C_{18}$ reversed phase HPLC column (5 μm, 150×2.1 mm) eluted with acetonitrile/methanol (80:20) with trifluoroacetic acid (0.1%) at a flow rate of 0.3 mL/min. UV monitoring at 295 nm allowed detection of γ- and α-tocopherol at 11.1 and 12.9 minutes, respectively.

Tocopherol Data Analysis. Data to create standard curves for γ- and α-tocopherol was generated by duplicate or triplicate analysis of standards prepared as described above (1, 2, 5, 10, 50, 100, and 200 μg/mL tocopherols). For each sample, the integration of peaks was generated from the chromatogram at 295 nm and the background (extracted pooled human serum) was subtracted. Curve fitting was performed in Microsoft Excel. Linear or weighted (1/x or $1/x^2$) standard curves of UV absorbance at 295 nm vs. concentration in μg/mL were generated. Generally, the linear range for quantitation for γ- and α-tocopherol was 1–100 μg/mL and the lower limit of quantitation (LLOQ) was 1 μg/mL. Tocopherol levels of samples from each study subject were calculated using the standard curve generated on the day of analysis.

CEHC Standards. Standard mixtures of γ- and α-CEHC (1:1) in water (50, 100, 250, 500, 1000, and 5000 ng/mL each) were prepared from stock solutions on each day of analysis. Each standard mixture (10 μL) was added to 90 μL of pooled human serum to produce samples used to generate the standard curves (5, 10, 25, 50, 100, 500 ng/mL CEHCs).

CEHC Extraction. Ascorbic acid in water (10 μL, 5 mg/ml) was added to each standard serum sample prepared as described above and to each study subject serum sample (100 μL) to stabilize CEHCs, and then 100 μL β-glucuronidase solution [7,500 units/mL in 10 mM potassium phosphate buffer (pH 6.8)] was added to each sample to liberate conjugated CEHCs. Following the incubation period of 30 mins. at 37° C., 800 μL of methanol containing 10 μg/mL BHT was added to precipitate protein and extract the CEHCs. After vortexing and centrifugation, each supernatant was transferred to a Centricon YM-30 or YM-50 membrane filtration device which had been prepared by addition of 1 mL of water. Extracts were then centrifuged at 3,700 rpm at 15° C. for 45 minutes to decontaminate the samples. Solvents were removed from the filtrate and the residue was resuspended in 100 μL 45% methanol-0.1% acetic acid containing 50 μg/mL ascorbic acid.

CEHC Analysis. Extracted CEHCs were analyzed by LC-MS (30 μL injection) using an Alltima $C_{18}$ reversed phase HPLC column (5 μm, 150×2.1 mm) eluted with a solvent gradient starting in water (0.1% HOAc)/methanol (55:45) for 1 min., followed by a linear gradient to 80% methanol at 10 mins. at a flow rate of 0.25 mL/min. These conditions were maintained until 15 mins. when a quick (0.5 min.) gradient to 100% methanol was used to wash the column (held until 25 mins.). Monitoring the separation by mass spectrometry using an electrospray ionization (ESI) source operating in the negative ion mode with selective ion monitoring (SIM) at 263.1 amu (γ-CEHC) and 277.1 (α-CEHC) allowed detection of γ- and α-CEHC at 12.9 and 13.8 mins, respectively.

CEHC Data Analysis. Data to create standard curves for γ- and α-CEHC were generated by duplicate or triplicate analysis of standards prepared as described above (5, 10, 25, 50, 100, 500 ng/mL). For each sample, the integration of peaks was generated from the SIM chromatogram at 263.1 amu (γ-CEHC) and 277.1 (α-CEHC), and the background (extracted pooled human serum) was subtracted. Curve fitting was performed in Microsoft Excel. Linear or weighted ($1/x$ or $1/x^2$) standard curves of SIM peak area vs. concentration in ng/mL were generated. Generally, the linear range for quantitation was 10–500 ng/mL or 5–500 ng/mL and the lower limit of quantitation (LLOQ) was 10 and 5 ng/mL for γ- and α-CEHC, respectively. CEHC levels of samples from each study subject were calculated using the standard curve generated on the day of analysis.

Example 5

Effects of Tocopherols on Inflammatory Mediators in Adults with End-stage Renal Disease Patients with end-stage renal disease (ESRD) who were on chronic hemodialysis were recruited for the study. The subjects were required to be between the ages of 30 and 60 and to have clinically acceptable hepatic function (transaminases<2 times normal and white blood cell (WBC) between 4.5–10.5K). Healthy age and gender-matched adults were also recruited for the study. All subjects gave informed consent, and the study protocol was approved by the Institutional Review Board of the participating clinic.

Patients were randomly assigned to receive either a single 600 mg dose of α-tocopherol or a γ/δ-tocopherol-rich mixed tocopherol preparation (defined below) ("Acute Phase"). After a 3–4 week washout period, patients received 300 mg/day for two weeks ("Chronic Phase"). The test articles were prepared in identical soft-gel capsules by standard methods in a contract GMP facility, containing either: "α-T"-95% d-α-tocopherol; or "γ/δ-T"-a γ-tocopherol enriched tocopherol mixture containing 60% d-γ-tocopherol, 28% d-δ-tocopherol, and 10% d-α-tocopherol.

Clinical parameters were assessed one day before and one and six days after the acute dose in the Acute Phase. For the Chronic Phase, clinical parameters were assessed at baseline and after one and two weeks treatment. Blood chemistries, CBC with differential and vital signs (weight, blood pressure, temperature and heart rate) were determined at every visit. Serum α-tocopherol (α-T), γ-tocopherol (γ-T), α-CEHC and γ-CEHC were analyzed by HPLC and LC-MS as described in Example 4 on blood taken at each visit. Serum CRP, and IL-6 and pre-albumin were measured at the start and end of the 2-week dosing phase of the study. At two visits, one day after the acute dose and another at the two-week time point in the second phase of the study, blood samples were drawn at the inception of dialysis and also just before the end of the dialysis session allowing assessment of the effects of dialysis on serum levels of the tocopherols and CEHCs. Patient health status and safety were assessed by physical examination, vital signs, clinical laboratory evaluations, and reports of adverse events throughout the study.

Analysis of data: Wilcoxon signed rank tests were performed for within-group comparisons and Mann-Whitney U test between groups. The Spearman rank correlation test was used to measure the association between serum CRP and IL-6. Analyses were carried out using Intercooled Stata 6.0 for Windows 98/95/NT (Stata Corporation, College Station, Tex.). Data are reported as means+/–SEM unless otherwise noted.

Results: Baseline serum y-tocopherol metabolite γ-CEHC levels were six-fold higher in the ESRD patients than in healthy controls (582.2 vs. 95.3 ng/ml); similarly, α-tocopherol serum α-CEHC levels were nearly 10-fold higher in ESRD patients than in the controls (72.3 vs. 7.4 ng/ml).

One day after the 600 mg γ/δ-T administration, γ-CEHC levels more than doubled in the ESRD group (730 to 1848 ng/ml) and increased seven-fold in the controls (67 to 348 ng/ml). Immediately post-dialysis, γ-CEHC had returned to baseline and when measured again five days later, γ-CEHC was near baseline in both the ESRD and the control groups.

After a 28-day washout period followed by 7 days of 300 mg γ/δT per day, serum γ-CEHC increased more than 4-fold in the ESRD group (749.2 to 3892.6 ng/ml), but rose no higher after another 7 days of treatment pre-dialysis (3395.4 ng/ml) and dropped by more than half post-dialysis (1521 ng/ml). In the control group, γ-CEHC increased from 67 to 347 ng/ml after one week and then rose no higher (280 ng/ml).

In contrast, there was no apparent change in α-CEHC in either the ESRD or control group after taking a single dose of the 600 mg αT. After a 28-day washout period followed by 7 days of 300 mg αT per day, serum α-CEHC increased more than 4-fold (from 56 to 267 ng/ml), and after another 7 days of treatment increased to 354 ng/ml. Post-dialysis α-CEHC levels dropped by more than half (152 ng/ml). In the control group, α-CEHC increased from 11 to 49 ng/ml after one week and then remained unchanged (36 ng/ml).

Inflammatory Markers: Serum C-reactive protein, IL-6 Median serum CRP decreased by 52% following two weeks of daily γ/δ-tocopherol dosing in the ESRD group (4.4 mg/L to 2.1 mg/L, p<0.02). Serum IL-6 levels decreased from 19.4 to 15.8 pg/ml and the change in IL-6 was positively correlated with the change in serum CRP levels over the two weeks of daily γ/δ-tocopherol dosing in the ESRD group (ρ=0.62, p=0.075)

The results of the present study, therefore, provide evidence of protective effects of a γ-tocopherol enriched tocopherol composition comprising δ-tocopherol in this at-risk patient population, by virtue of their CRP-lowering effects.

Further, this treatment did not suppress normal physiological increases in CRP in response to acute phase injury, as evidenced by data from a patient who underwent surgery during the two-week study (and whose data was therefore not included in the study results). Post-surgical CRP increased by more than 8-fold, as would be expected as a normal physiological response to such trauma, providing evidence that treatment in accordance with the present invention does not prevent the normal physiological rise in CRP associated with the acute phase response to injury or infection. Evidence that such an acute phase response is beneficial in fighting infection is provided by human C-reactive protein transgenic mouse. These transgenic mice have been shown to have lower mortality rates and decreased bacteremia when injected with *Streptococcus pneumoniae* as compared to wild-type mice (Szalai A J, et al., Clin Chem Lab Med 1999;37:265–70).

Example 6

Carrageenan-induced Rat Paw Edema Assay

Methods

Animal Preparation: Male Sprague-Dawley rats weighing between 175 to 200 g were used in this study. Animals were allowed free access to water and commercial rodent diet under standard laboratory conditions. Room temperature was maintained at 20–23° C. and room illumination is on a 12/12-hour light/dark cycle. Animals were acclimatized to the laboratory environment 5 to 7 days prior to the study.

Experimental Procedure

Each animal was treated by administration of vehicle, reference or test substance one hour prior to carrageenan injection, as follows: I.V. Infusion via Femoral Vein: Anesthesia was maintained by inhalation of 3.0% isoflurane (Aerrane, Front Dodge, Iowa) in oxygen throughout the entire procedure. The exterior site of the right femoral vein was shaved and sterilized prior to surgery. A 3-cm incision was made in the right groin region and the femoral vein was isolated. The femoral vein was temporarily ligated with a micro-vascular clip, and a small incision was made on the femoral vein to introduce and advance a polyethylene (PE-50) catheter (Becton. Dickinson and Co., Sparks, Md.). The catheter was secured in place with suture (silk 5/0, Carlisle Laboratories, Farmers Branch, Tex.). The other end of the catheter was attached to a syringe filled with the saline for the bolus injection. Using a hemostat, a pocket was made subcutaneously on the back of the animal so the PE catheter could be brought up to the exteriorization point between the shoulder blade for either a bolus injection or a continuous injection by an osmotic pump. Gavage Feeding: A standard rat gavage tube (Popper & Sons Inc, NY) was attached to a 3-cc hypodermic syringe. The animal was held in a vertical position. The feeding tube was placed into the mouth and then gently advanced until it reached the stomach. The content of the syringe was slowly delivered, and then the tube was withdrawn.

I.P. Injection: An awake rat is held in a standard hand held position. A 23 ¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

One hour post treatment each animal was anesthetized with 3.0% isoflurane (Aerrane, Front Dodge, Iowa) in oxygen and administered 100 μl of 1% Carrageenan Lambda type IV (Sigma Chemical Company, St. Louis, Mo.) suspension (freshly made, within 2–3 hours of use) in saline, into the intraplantar surface of the right hind paw. Paw edema was measured four hours after carrageenan injection, either by measuring the increase in paw volume using a plethysmometer or the increase in paw weight using a fine scale. Immediately prior to edema measurement, the animals were euthanized via $CO_2$ asphyxiation and 500 μl blood was withdrawn by cardiac puncture for later analysis. Paw volume was determined by the extent to which water was displaced by the paw from a pre-calibrated chamber. The volume of the left hind paw (control) was subtracted from the volume of the right hind paw (carrageenan-treated) to determine the volume of carrageenan-induced edema. To measure the weight difference between paws, both hind paws were removed and weighed separately. Edematous fluid was removed and tested for inflammatory markers, such as IL-6, using standard ELISA techniques known in the art.

Statistical Analysis

The difference of the weight or the volume or biomarker level between right and left paw was calculated for each animal for the analysis. Group data were presented as means+/−SEM, and $p<0.05$ is considered significant. Intergroup comparisons are carried out by unpaired student t test (between two groups) or one-way ANOVA followed by post hoc Bonferroni's multiple comparisons.

RESULTS

Gamma-tocopherol (3 days, 10–100 mg/kg/day oral pretreatment) produced significant reduction (42, $p<0.001$) in IL-6 present in edematous fluid tested by this method. Other non-alpha tocopherol enriched tocopherol compositions or non-alpha tocopherol metabolite enriched compositions can be tested in this model to determine reduction of IL-6.

The invention claimed is:

1. A method of reducing the level of IL-6 in an individual subject to an IL-6 associated inflammatory condition comprising administering to the individual an effective amount of non-alpha-tocopherol enriched tocopherol composition, wherein said non-alpha tocopherol is selected from the group consisting of gamma-tocopherol, beta-tocopherol and delta-tocopherol, and wherein said composition comprises less than 30% alpha-tocopherol.

2. The method of claim 1 wherein said non-alpha-tocopherol is gamma-tocopherol.

3. The method of claim 1 wherein said non-alpha tocopherol is beta-tocopherol.

4. The method of claim 1 wherein said non-alpha-tocopherol is delta-tocopherol.

5. The method of claim 1 wherein said composition further comprises a pharmaceutically acceptable carrier.

6. The method of claim 5 wherein said composition is formulated to be a topical composition.

7. The method of claim 1 wherein said inflammatory condition is an inflammatory skin condition.

8. The method of claim 1 wherein said composition comprises less than 25% alpha-tocopherol.

9. The method of claim 8 wherein said composition comprises less than 20% alpha-tocopherol.

10. The method of claim 9 wherein said composition comprises less than 15% alpha-tocopherol.

11. The method of claim 10 wherein said composition comprises less than 10% alpha-tocopherol.

12. The method of claim 11 wherein said composition comprises less than 5% alpha-tocopherol.

13. A method of reducing the level of IL-6 in an individual subject to an IL-6 associated inflammatory condition comprising administering to the individual an effective amount of non-alpha-tocopherol enriched tocopherol composition, wherein said composition comprises at least 60% gamma-tocopherol, at least 28% delta-tocopherol and no greater than 10% alpha-tocopherol.

14. A method of reducing the level of IL-6 in an individual subject to an IL-6 associated inflammatory condition comprising administering to the individual an effective amount of a metabolite of a non-alpha-tocopherol selected from the group consisting of a beta-tocopherol metabolite, a gamma-tocopherol metabolite and a delta-tocopherol metabolite.

15. The method of claim 14 wherein said non-alpha-tocopherol is a gamma-tocopherol metabolite.

16. The method of claim 15 wherein said gamma-tocopherol metabolite is 2,7,8-trimethyl-2-(2'-carboxyethyl)-6-hydroxychroman (gamma-CEHC).

17. The method of claim 14 wherein said non-alpha tocopherol is a beta-tocopherol metabolite.

18. The method of claim 17 wherein said beta-tocopherol metabolite is 2,5,8-trimethyl-2-(2-carboxyethyl)-6-hydroxychroman (beta-CEHC).

19. The method of claim 14 wherein said non-alpha-tocopherol is a delta-tocopherol metabolite.

20. The method of claim 19 wherein said delta-tocopherol metabolite is 2,8,-dimethyl-2-(2-carboxyethyl)-6-hydroxychroman (delta-CEHC).

* * * * *